US012773224B2

(12) United States Patent
Kidman et al.

(10) Patent No.: US 12,773,224 B2
(45) Date of Patent: Oct. 27, 2026

(54) SYSTEMS AND METHODS FOR AUGMENTATION OF A VERTEBRAL BODY

(71) Applicant: Stryker Corporation, Kalamazoo, MI (US)

(72) Inventors: Beau Michael Kidman, Kalamazoo, MI (US); Christopher Scott Brockman, Kalamazoo, MI (US); Gabriel James Harshman, Portage, MI (US)

(73) Assignee: Stryker Corporation, Portage, MI (US)

( * ) Notice: Subject to any disclaimer, the term of this patent is extended or adjusted under 35 U.S.C. 154(b) by 586 days.

(21) Appl. No.: 18/027,814

(22) PCT Filed: Sep. 22, 2021

(86) PCT No.: PCT/US2021/051516
§ 371 (c)(1),
(2) Date: Mar. 22, 2023

(87) PCT Pub. No.: WO2022/066743
PCT Pub. Date: Mar. 31, 2022

(65) Prior Publication Data

US 2023/0338045 A1 Oct. 26, 2023

Related U.S. Application Data

(60) Provisional application No. 63/081,449, filed on Sep. 22, 2020.

(51) Int. Cl.
*A61B 17/17* (2006.01)
*A61B 10/02* (2006.01)
(Continued)

(52) U.S. Cl.
CPC ........ *A61B 17/1757* (2013.01); *A61B 10/025* (2013.01); *A61B 17/1671* (2013.01); *A61B 2018/00339* (2013.01)

(58) Field of Classification Search
CPC ............ A61B 17/8819; A61B 17/8802; A61B 17/8805; A61B 17/1757; A61B 17/1671; A61B 17/1642
See application file for complete search history.

(56) References Cited

U.S. PATENT DOCUMENTS 6,547,432 B2 4/2003 Coffeen et al.
7,658,537 B2 2/2010 Coffeen et al.
(Continued)

FOREIGN PATENT DOCUMENTS

EP 3081252 A1 10/2016
WO 2009065085 A1 5/2009
(Continued)

OTHER PUBLICATIONS

Davis, MD, A. David/Stryker, "Sports Medicine—Evidence Matters—Cartilage Regrowth on Chondral Lesion Using MicroFX", 1000902206 Rev A, 2016, 2 pages.
(Continued)

*Primary Examiner* — Amy R Sipp
(74) *Attorney, Agent, or Firm* — Howard & Howard Attorneys PLLC

(57) ABSTRACT

Systems and methods for augmenting a vertebral body. The system includes an access cannula, an introducer device, a sheath device, and a treatment device. The introducer device may be moved from unconstrained state to a constrained state in which a pulling element is tensioned. The access cannula may initially prevent the shaft sheath from assuming a curve, after which the introducer device and the sheath device may be advanced relative to the access cannula to assume the curve within the vertebral body. An actuator of the introducer device may include a resilient arm configured to resiliently deflect such that a lock head releasably engages a feature of a handle of the introducer device. A spacer lock facilitates proximal movement of the sheath relative to the
(Continued)

access cannula so as to expose the treatment device within the vertebral body at a location offset from a longitudinal axis of the access cannula.

16 Claims, 21 Drawing Sheets

(51) Int. Cl.
*A61B 17/16* (2006.01)
*A61B 18/00* (2006.01)

(56) References Cited

U.S. PATENT DOCUMENTS

| | | | |
|---|---|---|---|
| 8,894,658 B2 | 11/2014 | Linderman et al. | |
| 8,961,553 B2 | 2/2015 | Hollowell et al. | |
| 9,579,130 B2 | 2/2017 | Oglaza et al. | |
| 9,839,443 B2 | 12/2017 | Brockman et al. | |
| 10,441,295 B2 | 10/2019 | Brockman et al. | |
| 2007/0055260 A1 | 3/2007 | Cragg | |
| 2008/0028192 A1 | 1/2008 | Sugimoto | |
| 2010/0036381 A1* | 2/2010 | Vanleeuwen | A61B 17/8805 606/93 |
| 2013/0006232 A1 | 1/2013 | Pellegrino et al. | |
| 2013/0072941 A1* | 3/2013 | Tan-Malecki | A61B 17/8819 606/94 |
| 2014/0074102 A1 | 3/2014 | Mandeen et al. | |
| 2016/0175019 A1 | 6/2016 | Henniges et al. | |
| 2019/0038345 A1 | 2/2019 | Pellegrino et al. | |
| 2020/0060741 A1 | 2/2020 | Brockman et al. | |
| 2020/0383707 A1 | 12/2020 | Kidman et al. | |

FOREIGN PATENT DOCUMENTS

| | | |
|---|---|---|
| WO | 2011137377 A1 | 11/2011 |
| WO | 2019200091 A1 | 10/2019 |

OTHER PUBLICATIONS

International Search Report for Application No. PCT/US2021/051516 dated Apr. 19, 2022, 3 pages.

Partial International Search Report for Application No. PCT/US2021/051516 dated Feb. 24, 2022, 3 pages.

Stryker, "MicroFX OCD Osteochondral Drilling System Brochure", MFOCD-B-1 Rev. B, 2016, 3 pages.

* cited by examiner

SYSTEMS AND METHODS FOR AUGMENTATION OF A VERTEBRAL BODY

PRIORITY CLAIM

This is a national entry of International Application No. PCT/US2021/051516, filed Sep. 22, 2021, which claims priority to and all the benefits of U.S. Provisional Application No. 63/081,449, filed Sep. 22, 2020, the entire contents of each being hereby incorporated by reference.

BACKGROUND

A common source of back pain is a vertebral compression fracture in which a weakened or injured vertebral body loses height or collapses. The weakening of the vertebral body may be due to acute injury or, more often, degenerative changes such as osteoporosis. The compression fractures often appear on lateral radiographs as wedge deformities with greater loss of height anteriorly.

One treatment modality includes vertebral augmentation in which the height of the vertebral body is elevated or restored, and stabilized at the elevated or restored height. A vertebroplasty includes delivering curable material, for example a bone cement, within an interior of the vertebral body. The material interdigitates with cancellous bone and cures to stabilize the vertebral body. A kyphoplasty includes creating a cavity within the interior of the vertebral body by compressing the cancellous bone with an expandable member such as a balloon, and delivering the curable material into the cavity. The expandable member may facilitate elevating or restoring the height of the vertebral body.

Accessing the interior of the vertebral body often includes percutaneously placing an access cannula through a pedicle of the vertebra. Owing to the structure of the vertebra, accessing a location on the contralateral side of the vertebral body is not especially feasible with straight instrumentation. As such, one existing kyphoplasty technique employs a bipedicular approach in which two access cannulas are placed, followed by two expandable members each positioned ipsilaterally within the interior of the vertebral body. The bipedicular approach undesirably requires twice the trauma to tissue, and often requires twice the instrumentation.

Of particular interest is a unipedicular approach in which the instrumentation is designed to access locations of the interior of the vertebral body offset from a longitudinal axis of the access cannula, including locations on the contralateral side of the vertebral body. One exemplary system utilizing the unipedicular approach is disclosed in commonly owned U.S. Pat. No. 8,894,658, issued Nov. 25, 2014, hereby incorporated by reference in its entirety, and sold under the tradename Avaflex by Stryker Corporation (Kalamazoo, Mich.). While the disclosure realizes the benefits of the unipedicular approach, there is further need in the art for systems and methods for off-axis vertebral augmentation.

SUMMARY

A first aspect of the present disclosure is directed to method of augmenting a vertebral body. A distal end of an access cannula is positioned within the vertebral body such that a lumen of the access cannula provides access to an interior region of the vertebral body along a longitudinal axis. A shaft of the introducer device and the sheath are directed to within the access cannula such that the distal portion of the introducer device and the flexible region of the sheath remains within the access cannula. The introducer device is in an unconstrained state in which a pulling element is at a first tension. Thereafter, an input to an actuator to move the introducer device from the unconstrained state to a constrained state in which the pulling element is at a second tension greater than the first tension. The access cannula prevents the distal portion of the shaft and the distal portion of the sheath from assuming a curve from the longitudinal axis. Thereafter, the introducer device and the sheath device are advanced relative to the access cannula with the introducer device in the constrained state such that the distal portion of the introducer device and the distal portion of the sheath assume the curve within the vertebral body with advancement beyond the distal end of the access cannula.

In certain implementations, the distal portion of the introducer device and the flexible region of the sheath and configured to plunge through cancellous bone within the vertebral body while assuming the curve. Prior to plunging, a distal end of the sheath may be positioned in registration with the distal end of the access cannula. Indicia disposed on the sheath may be aligned with a hub of the access cannula so as to position the distal end of the distal portion in registration with the distal end of the access cannula.

In certain implementations another input may be provided to the actuator to move or return the introducer device from the constrained state to the unconstrained state. The introducer device may be removed from the sheath device. In particular, the pulling element being at the first tension in the unconstrained state provides for removal of the introducer device from the sheath with the flexible region of the sheath remaining curved within the vertebral body. The cancellous bone of the vertebral body may at least partially support the curve. Should the curve not be positioned in the desired orientation, for example, the introducer device may be redirected through the sheath device. Thereafter, still another input to the actuator to move the introducer device from the unconstrained state to the constrained state so as to reestablish the curve of the flexible region to selectively adjust the orientation of the curve. The adjustment may not require the removal of the sheath device from the access cannula. Thereafter, the introducer device may be returned to the unconstrained state, and removed from the sheath device.

In certain implementations, the system includes a spacer lock defining an aperture and including legs defining at least one slot. The legs of the spacer lock may be engaged with a cannula hub of the access cannula such that the aperture is aligned with the lumen. A sheath hub of the sheath is disposed within the slot(s). A treatment device may be directed through the aperture to within the sheath. The treatment device is flexible to bend along the curve of the flexible region of the sheath disposed within the vertebral body. The sheath hub may be proximally moved within the slot(s) of the spacer lock with corresponding movement of the sheath, thereby exposing the treatment device at a target location within the vertebral body. Augmentation of tissue of the vertebral body may be performed at the target location with the treatment device. The treatment device may be one of a cavity-forming device configured to displace tissue, an electrode probe configured to ablate tissue, a drill device for cutting tissue, and a tissue capturing device for tissue biopsy, among others. An input may be provided to the lock actuator of the spacer lock to disengage the lock actuator from a shaft of the treatment device. The treatment device may be moved within the aperture of the spacer lock to selectively adjust a position of the treatment device relative to the access cannula. The input may then be removed to reengage the lock mechanism and the shaft of the treatment device, thereby preventing further movement of the treatment device relative to the access cannula.

In certain implementations, the treatment device may be removed from the sheath. A curved path remains in the vertebral body that is along the curve previously assumed by the introducer device. The flexible region of the sheath is advanced relative to the distal end of the access cannula. A preformed bend of a polymeric sleeve associated with the flexible region of the sheath facilitates the sheath following the curved path. Curable material may be delivered through the sheath to within the vertebral body. The polymeric sleeve may also prevent egress of the curable material through articulating features of the metal tube.

A second aspect of the present disclosure is directed to system of augmenting a vertebral body. An access cannula includes a cannula hub, and a cannula shaft extending from the cannula hub. The cannula shaft includes a distal end positionable within the vertebral body and defining a lumen along a longitudinal axis. An introducer device includes an actuator, a shaft, and a pulling element. The actuator configured to receive an input from a user. The shaft includes a proximal portion that is rigid, and a distal portion that is articulable. The pulling element is coupled to the actuator and configured to be tensioned to move the introducer device from an unconstrained state in which the distal portion is oriented along the longitudinal axis, and a constrained state in which the distal portion is configured to assume a curve away from the longitudinal axis. The shaft is removably disposed within a sheath. The sheath includes a metal tube having articulating features to define a flexible region configured to extend along the distal portion of the shaft, and a polymeric sleeve coupled to the metal tube and extending between opposing ends of the flexible region. The polymeric sleeve is configured to prevent egress of curable material being delivered through the sheath through the articulating features.

In certain implementations, the polymeric sleeve is disposed within the metal tube. Alternatively, metal tube may be disposed within the polymeric sleeve. In particular, the polymeric sleeve may extend over the proximal portion to a sheath hub of the sheath. The polymeric sleeve may include a preformed bend. A helical cut pattern may be disposed within the flexible region of the metal tube.

In a third aspect of the disclosure is directed to a method of augmenting a vertebral body with the system according to the second aspect of the disclosure, and optionally, any of its corresponding implementations. The system of the second aspect of the disclosure, and optionally, any of its corresponding implementations, may be used to perform the method according to the first aspect of the disclosure.

A fourth aspect of the disclosure is directed to a system for augmenting a vertebral body. An access cannula includes a cannula hub, and a cannula shaft extending from the cannula hub. The cannula shaft includes a distal end positionable within the vertebral body distal portion configured to assume a curve when deployed beyond the distal end of the cannula shaft. A sheath device includes a sheath hub, and a sheath extending from the sheath hub. The shaft is removably disposed within the sheath. A spacer lock is configured to facilitate proximal movement of the sheath relative to the access cannula. The spacer lock includes legs configured to be removably positioned in abutment with an engagement surface of the access cannula, and defining at least one slot sized and shaped to slidably receive the sheath hub and prevent rotation of the sheath relative to the spacer lock.

In certain implementations, the spacer lock is configured to rest upon the engagement surface under influence of gravity without an additional coupling mechanism. The cannula hub may include handles spaced proximal to the engagement surface. The legs and the handles are positioned in an interlocking arrangement such that opposing aspects of at least one of the handles may prevent rotation of the spacer lock relative to the access cannula. The sheath hub being disposed within the slots prevents rotation of the sheath relative to the spacer lock, and optionally relative to the access cannula.

In certain implementations, the spacer lock further includes a lock actuator configured to receive an input from a user, and a lock mechanism configured to releasably engage the shaft of a treatment device in response to the lock actuator receiving the input so as to selectively permit movement of the treatment device relative to the sheath device. The lock mechanism may include a torsion spring configured to bias the lock actuator a closed state in which the lock mechanism engages the shaft of the treatment device. The lock mechanism may include a disc having thinned regions defining slots and an opening. The thinned regions are configured to resiliently deflect under force from the input to the lock actuator. The lock mechanism is configured to be in a natural or closed state in which a size of the opening is slightly smaller than an outer diameter of the shaft of the treatment device.

In some implementations, the spacer lock of the fourth aspect may be included with the system according to the second aspect of the disclosure, and optionally, any of its corresponding implementations.

A fifth aspect of the disclosure is directed to a system for augmenting a vertebral body. An access cannula includes a cannula hub, and a cannula shaft extending from the cannula hub. The cannula shaft includes a distal end positionable within the vertebral body distal portion configured to assume a curve when deployed beyond the distal end of the cannula shaft. A sheath device includes a sheath hub, and a sheath extending from the sheath hub. The shaft is removably disposed within the sheath. A spacer lock configured to facilitate proximal movement of the sheath relative to the access cannula. The spacer lock includes a lock mechanism defining an aperture sized to slidably receive the tube, and a lock actuator coupled to the lock mechanism. The lock actuator is configured to receive an input from a user to selectively permit movement of a cavity-forming device relative to the access cannula or the sheath device.

In certain implementations, the lock mechanism biased to a closed state. The spacer lock may include legs, and flanges may extend radially outwardly from the legs to provide a proximal surface for accommodating a thumb of a hand of a user. The cannula hub may include handles with the legs and the handles positioned in an interlocking arrangement to prevent rotation of the spacer lock relative to the access cannula.

In some implementations, the spacer lock of the fifth aspect of the disclosure may be included with the system according to the second aspect, and optionally, any of its corresponding implementations.

A sixth aspect of the disclosure is directed to a method of augmenting a vertebral body. A distal end of an access cannula is directed within the vertebral body to provide access to an interior region of the vertebral body along a longitudinal axis. A shaft of the introducer device and a sheath are directed to within the access cannula. The introducer device is operated to cause a distal portion of the shaft and a flexible region of the sheath to assume a curve within the interior region of the vertebral body. The shaft is removed from the sheath. The flexible region of the sheath remains along the curve. Thereafter, the sheath hub is aligned with at least one slot of the spacer lock. Legs of the spacer lock are positioned on an engagement surface of the access cannula such that the spacer lock is disposed within the slot(s). Rotation of the sheath relative to the spacer lock is prevented. The sheath hub is moved proximally within the slot(s) to move the sheath relative to the access cannula, and optionally relative to a treatment device.

In certain implementations, an expandable member and a tube of a cavity-forming device are directed through an aperture in the spacer lock such that the expandable member is in registration with a distal end of the sheath and the hub contacts the spacer lock. The sheath hub may be moved within the slot(s) towards the hub so as to expose the expandable member beyond the distal end of the sheath. An input may be provided to a lock actuator of the spacer lock to disengage the lock actuator from the tube of the cavity-forming device. The tube may be moved within the aperture of the spacer lock to selectively adjust a position of the expandable member relative to the access cannula or the sheath. The spacer lock and the cavity-forming device may be decoupled from the access cannula, thereby exposing a Luer fitting on the sheath hub.

In certain implementations, an electrode shaft is directed through an aperture in the spacer lock such that a probe of an electrode probe is in registration with a distal end of the sheath and the electrode hub contacts the spacer lock. The sheath hub may be moved within the slot(s) towards the electrode hub so as to expose the probe beyond the distal end of the sheath.

In some implementations, the spacer lock of the sixth aspect may be included with the system according to the second aspect, and optionally, any of its corresponding implementations.

A seventh aspect of the disclosure is directed to an introducer device for augmenting a vertebral body. A handle defining a proximal opening and includes a ramp, and a retention feature adjacent the ramp. A shaft includes a proximal portion that is rigid and defining a longitudinal axis, and a distal portion that is articulable. The shaft is configured to be removably disposed within a sheath. A pulling element is coupled to the distal portion and configured to be tensioned to move the introducer device from an unconstrained state in which the distal portion is oriented along the longitudinal axis, and a constrained state in which the distal portion is configured to assume a curve away from the longitudinal axis. An actuator is pivotably coupled to the handle and coupled to the pulling element. The actuator includes a control member defining a control surface, a resilient arm extending from the control member in a direction opposite the control surface so as to be disposed within the handle, and a lock head at an end of the resilient arm. The control surface is configured to receive an input from a user to pivotably move the control member towards the handle and the lock head towards the proximal opening. The resilient arm is configured to deflect as the lock head moves along the ramp, and return to an original state for releasable engagement between the lock head and the retention feature so as to lock the introducer device in the constrained state.

In certain implementations, the lock head extends through the proximal opening when the lock head engages the retention feature. The lock head may include a proximally-facing protrusion having a release surface configured to be actuated by a thumb of a hand of a user.

In some implementations, the actuator of the seventh aspect may be included with the introducer device of the systems according to the second, fourth, fifth and sixth aspects, and optionally, any of their corresponding implementations. The handle may be formed as a pistol grip having a frame from which the shaft extends. The frame includes shoulders defining a void configured to receive removably the sheath hub so as to prevent rotation of the sheath device relative to the introducer device. The pistol grip may include a handle and define a proximal surface of the handle. The proximal surface may be flattened and/or at least substantially planar so as to receive an impact from a surgical mallet. The handle may include indicia disposed on the proximal surface and configured to identify a direction of the curve of the distal portion with the introducer device in the constrained state.

An eighth of the disclosure is directed to a method of augmenting a vertebral body. A distal end of an access cannula may be positioned within the vertebral body to provide access to an interior region of the vertebral body along a longitudinal axis. A handle of the introducer device is grasped. A shaft of the introducer device and the sheath are directed within the access cannula such that the distal portion of the introducer device and the distal portion of the sheath are beyond the distal end of the access cannula. The introducer device is operated by pivoting the control member relative to the handle to cause the pulling element to be tensioned to move the introducer device from an unconstrained state in which the distal portion of the shaft is oriented along the longitudinal axis, and a constrained state in which the distal portion is configured to assume a curve away from the longitudinal axis. A ramp of the handle is deflected as the resilient arm moves along the ramp and engages a retention feature of the handle. A release surface extending through the proximal opening is depressed to disengage the lock head from the retention feature to move the introducer device from the constrained state to the unconstrained state.

In some implementations, the method of the eighth aspect may be included with the systems according to the second, fourth, fifth, sixth and seventh aspects, and optionally, any of their corresponding implementations.

A ninth aspect of the disclosure is directed to a sheath device for a system for augmenting a vertebral body. A sheath includes a proximal portion extending from a sheath hub along a longitudinal axis and comprising metal, and a distal portion comprising polymeric material. The proximal portion is coupled to the distal portion at an interface including a plurality of protrusions on each of the proximal portion and the distal portion configured to engage one another and provide a constant inner diameter and a constant outer diameter across the interface.

In certain implementations, the plurality of protrusions is disposed equiangularly about the longitudinal axis. Each of the plurality of protrusions may include a thinned region widening into a bulbous or circular profile. Alternatively, each of the plurality of protrusions on the proximal portion comprises a barb. Alternatively, each of the plurality of protrusions of the proximal portion comprises a tine that is wavy in shape.

In some implementations, the sheath of the ninth aspect may be included with the systems according to the second, fourth, fifth, sixth and seventh aspects, and optionally, any of their corresponding implementations.

A tenth aspect of the disclosure is directed to a system for augmenting a vertebral body. An access cannula includes a cannula hub, and a cannula shaft extending from the cannula hub. The cannula shaft includes a distal end positionable within the vertebral body and defining a lumen along a longitudinal axis. An introducer device includes an actuator, a shaft, and a pulling element. The actuator configured to receive an input from a user. The shaft includes a proximal portion that is rigid, and a distal portion. The pulling element is coupled to the actuator and to the distal portion. The pulling element configured to be tensioned to move the introducer device from an unconstrained state in which the distal portion is oriented along the longitudinal axis, and a constrained state in which the distal portion is configured to assume a curve away from the longitudinal axis. The shaft is removably disposed within a sheath. The sheath includes a distal end, a flexible region configured to be positioned along the distal portion of the shaft, and indicia disposed on the sheath. The access cannula and the introducer device have complementary lengths such that, when the indicia is in alignment with a proximal end of the cannula hub, the distal end of the sheath is in registration with the distal end of the access cannula.

In some implementations, the indicia of the tenth aspect may be included with the systems according to the second, fourth, fifth, sixth, seventh and ninth aspects, and optionally, any of their corresponding implementations.

An eleventh aspect of the present disclosure is directed to a method of augmenting a vertebral body. A distal end of the access cannula is positioned within the vertebral body to provide access to an interior region of the vertebral body along a longitudinal axis. The shaft of the introducer device and the sheath are directed beyond the access cannula. The introducer device is operated to cause the distal portion of the shaft and the flexible region of the sheath to assume a curve within the interior region of the vertebral body. The introducer device is removed from the sheath device with the flexible region of the sheath remaining in the curve. A drill device is directed through the sheath device and resecting tissue within the vertebral body, thereby leaving a bore. The drill device is removed from the sheath device.

In certain implementations, an electrode shaft of an electrode probe is directed through the sheath. A probe may be exposed beyond the distal end of the sheath and within the bore. The probe is operated to ablate tissue within the vertebral body. An expandable member is directed through the sheath to be exposed beyond the distal end of the sheath and within the bore. The expandable member may be directed into the bore before or after ablation of the tissue. The expandable member may be inflated to provide a cavity within the vertebral body. The expandable member is deflated, and then removed from the sheath. Curable material through the sheath to within the cavity of the vertebral body.

In some implementations, the drill device, the electrode probe, and/or the cavity-forming device of the method according to the eleventh aspect may be included with the systems according to the second, fourth, fifth, sixth, seventh, ninth and tenth aspects, and optionally, any of their corresponding implementations.

A twelfth aspect of the present disclosure is directed to method of augmenting a vertebral body. A distal end of an access cannula is positioned within the vertebral body to provide access to an interior region of the vertebral body along a longitudinal axis. A shaft of an introducer device and a sheath is directed beyond the access cannula. The introducer device is operated to cause the distal portion of the shaft and the flexible region of the sheath to assume a curve within the interior region of the vertebral body. The introducer device is removed from the sheath device with the flexible region of the sheath remaining in the curve. A biopsy device is directed through the sheath device and capture a tissue sample within the vertebral body. The biopsy device is removed from the sheath device.

In some implementations, the biopsy device of the method according to the twelfth aspect may be included with the systems according to the second, fourth, fifth, sixth, seventh, ninth, tenth aspects and eleventh, and optionally, any of their corresponding implementations.

A thirteenth aspect of the present disclosure is directed to method of augmenting a bone. A distal end of an access cannula is positioned within the bone to provide access to an interior region of the bone along a longitudinal axis. A shaft of an introducer device and a sheath is directed beyond the access cannula. The introducer device is operated to cause the distal portion of the shaft and the flexible region of the sheath to assume a curve within the interior region of the bone. The introducer device is removed from the sheath device with the flexible region of the sheath remaining in the curve. An electrode shaft through the sheath, and the probe of the electrode device is exposed beyond the distal end of the sheath. The probe is operated to ablate tissue within the bone.

In certain implementations the bone is one of a vertebral body, a cranium, a long bone, and an ilium. The methods and systems according to the first through twelfth aspects may be operable to augment any bone of the body.

In certain implementations, methods and systems according to the first through thirteenth aspects may be operable to augment non-osseous anatomy, for example, ear, nose, and throat (ENT) or other difficult to access anatomy with straight instrumentation.

BRIEF DESCRIPTION OF THE DRAWINGS

Advantages of the present invention will be readily appreciated as the same becomes better understood by reference to the following detailed description when considered in connection with the accompanying drawings.

DETAILED DESCRIPTION

Figure 1:
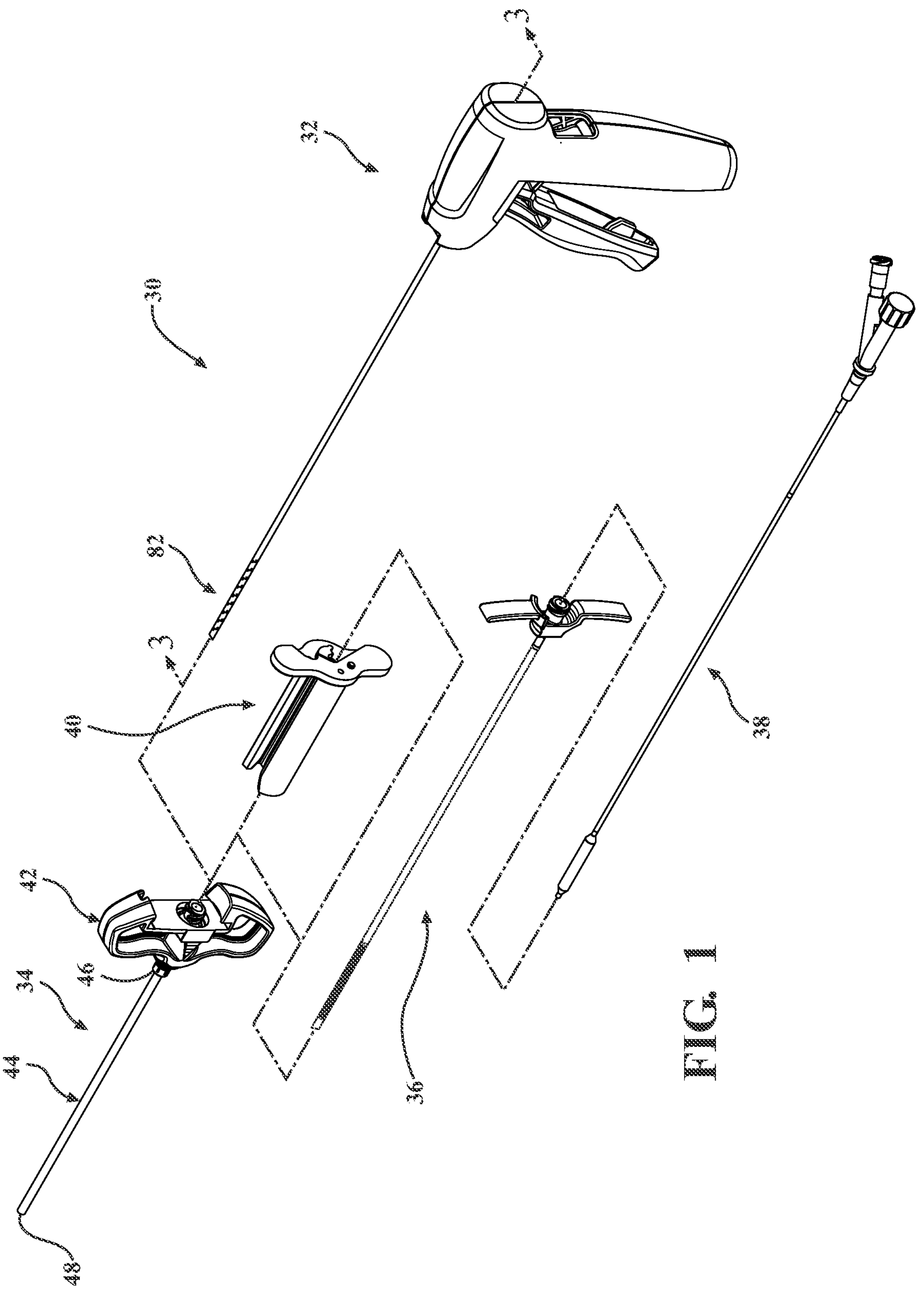
FIG. 1 shows a system for augmenting anatomy, for example, a vertebral body.

FIG. 1 shows a system 30 for augmenting anatomy. The system 30 includes an introducer device 32, an access cannula 34, and a sheath device 36. The system 30 may further include a treatment device (e.g., a cavity-forming device 38) and a spacer lock 40. As schematically represented by the broken lines of FIG. 1, the certain components of the system 30 are removably couplable to and/or deployable through one another in a manner that facilitates off-axis access within the anatomy of interest. An exemplary procedure to be described throughout the present disclosure is augmentation of vertebral body for performing a vertebroplasty, kyphoplasty, ablation, biopsy, drilling and/or other related procedure. In certain implementations, the system 30 may be configured to augment other bones of the body, for example, a cranium, a long bone, and an ilium. Alternatively, the system 30 may be configured to augment non-osseous anatomy, for example, ear, nose, and throat (ENT) or other difficult to access anatomy with straight instrumentation.

The access cannula 34 includes a cannula hub 42, and a cannula shaft 44 extending from the cannula hub 42. The cannula shaft 44 includes a proximal end 46 coupled to the cannula hub 42, and a distal end 48 opposite the proximal end 46. The cannula shaft 44 may be straight and define a lumen (not identified) extending between the proximal and distal ends 46, 48 such that the cannula shaft 44 is tubular in shape. The cannula shaft 44 may comprise or be formed from biocompatible materials with sufficient mechanical properties to maintain integrity as the cannula shaft 44 is driven through the pedicle of the vertebra. The system 30 may include a trocar (not shown) removably positioned within the cannula shaft 44 during placement of the distal end 48 of the cannula shaft 44 into the vertebral body. The trocar may include a length slightly greater than a length of the cannula shaft 44 such that a sharp tip of the trocar pierces the cortical bone of the cortical rim, and the trocar prevents coring of tissue within the lumen of the cannula shaft 44. Once the distal end 48 of the cannula shaft 44 is positioned within the vertebral body, the trocar is removed. The access cannula 34 provides a working channel to within the interior region of the vertebral body along a longitudinal axis defined by the cannula shaft 44. The cannula hub 42 is exposed above the tissue overlying the vertebra, and certain components of the system 30 are configured to be directed through the working channel of the access cannula 34.

Figure 2:
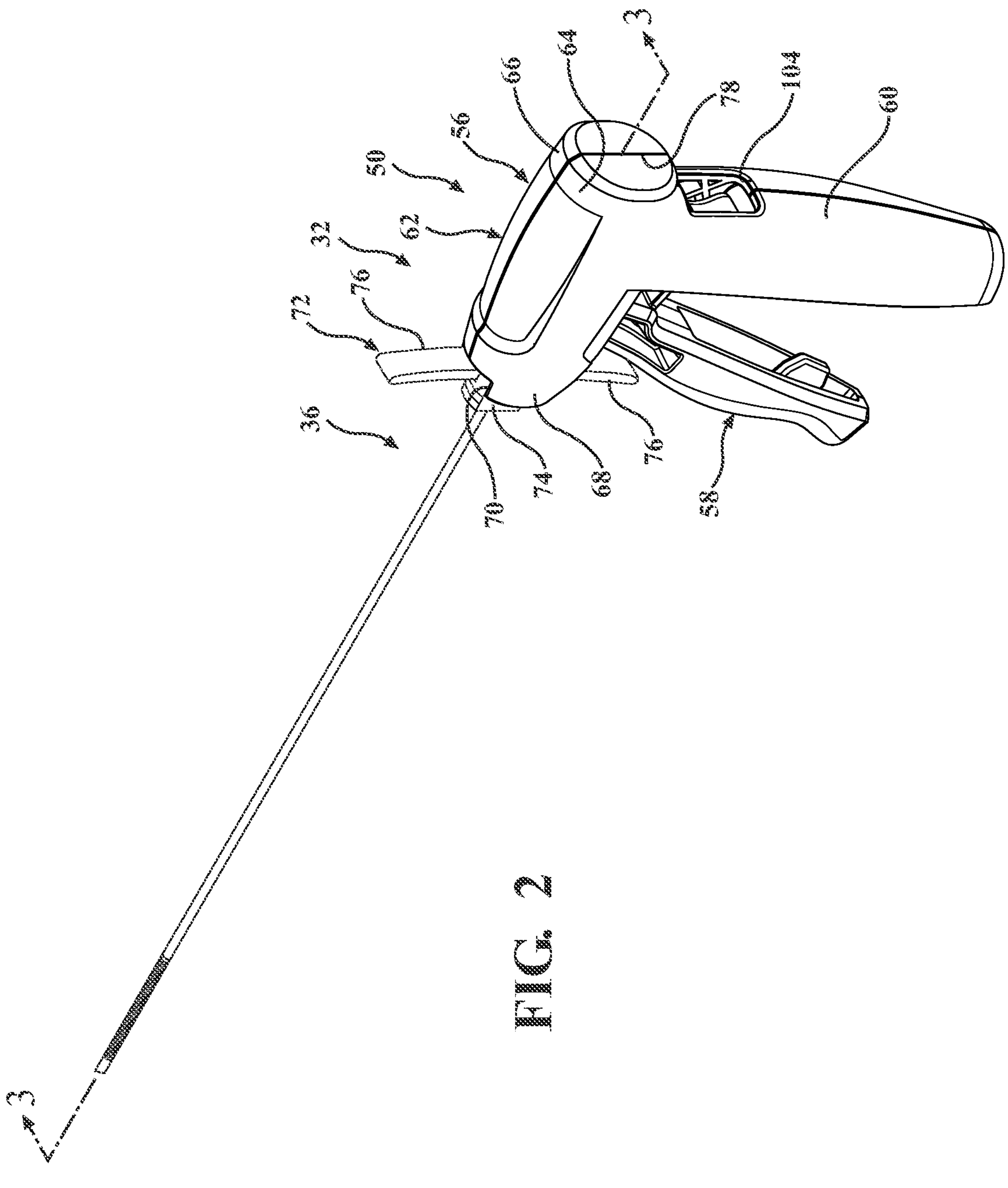
FIG. 2 is a rear perspective view of an introducer device in an unconstrained state, and a sheath device.
Figure 3:
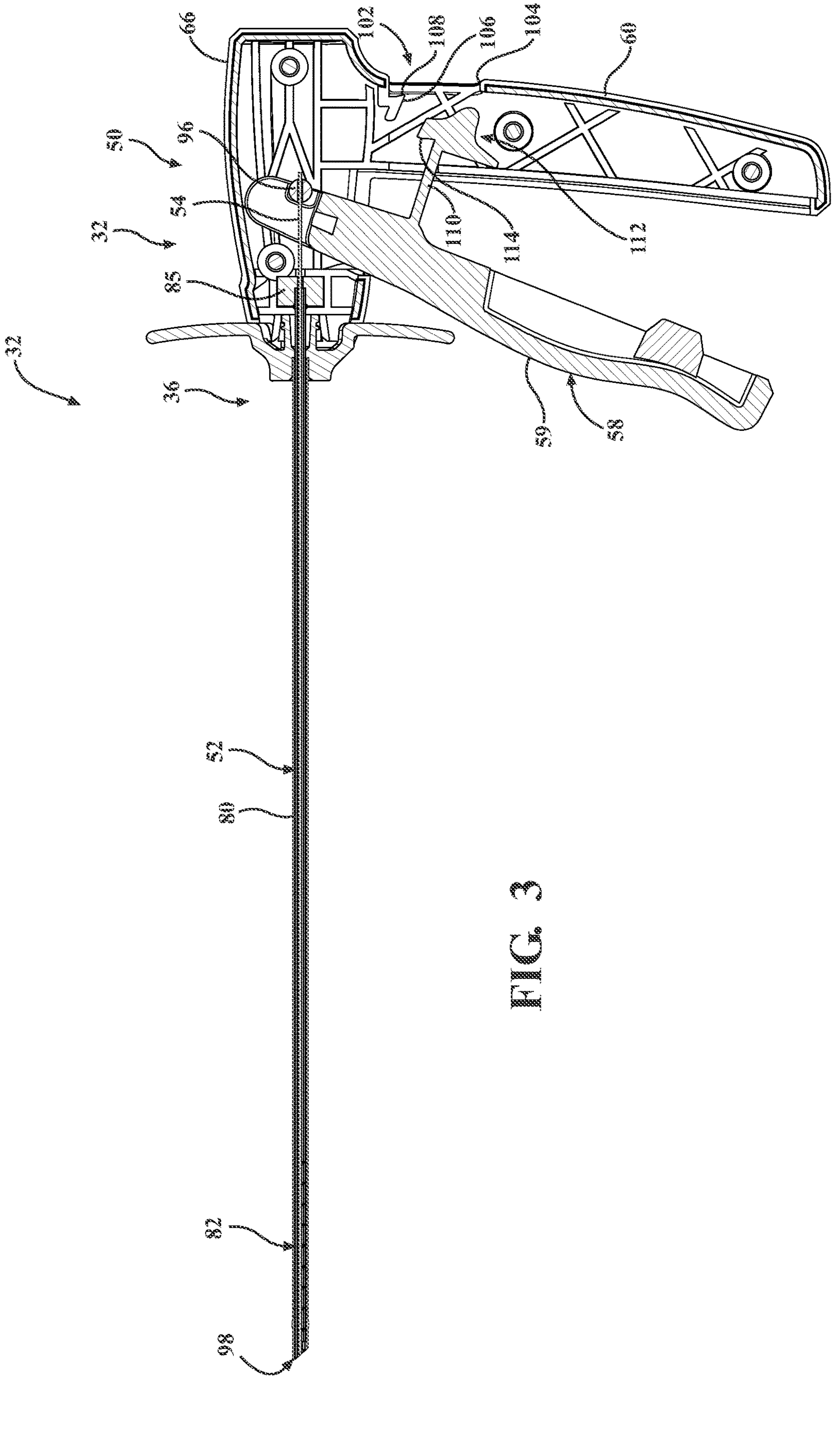
FIG. 3 is an elevational sectional view of the introducer device and the sheath device of FIG. 2 taken along section lines 3-3.
Figure 4:
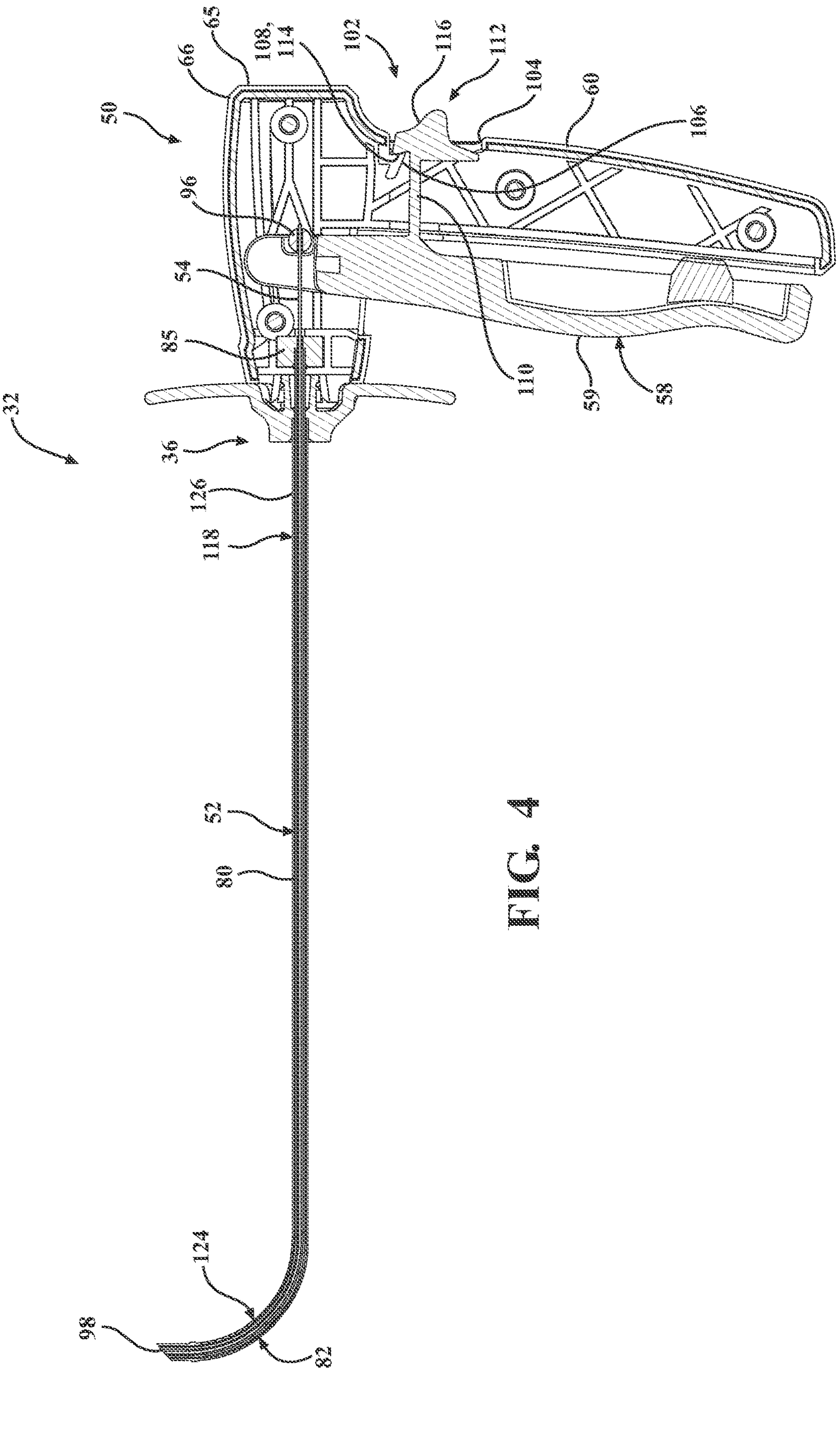
FIG. 4 is another sectional view of the introducer device and the sheath device in a constrained state.

The introducer device 32—to which the sheath device 36 may be removably coupled—may be directed within or through the access cannula 34. The introducer device 32 may be actuated to form a curved path within the vertebral body with advancement of the introducer device 32 beyond the access cannula 34. With reference to FIGS. 2-4, the introducer device 32 includes an actuator 50, and a shaft 52 extending from the actuator 50. The actuator 50 is configured to receive an input from a practitioner or user to actuate the introducer device 32 from an unconstrained state in which the shaft 52 of the introducer device 32 is straight and may be inserted or removed from the cannula shaft 44 of the access cannula 34, respectively. The introducer device 32 is actuated from the unconstrained state to a constrained state in which a distal portion 82 of the shaft 52 is urged away from the longitudinal axis. FIGS. 2 and 3 show the introducer device 32 in the unconstrained state, and FIG. 4 shows the introducer device 32 in the constrained state. The actuator 50 includes a housing 56, and a control member 58 movably coupled to the housing 56. The illustrated implementation shows the housing 56 and the control member 58 in a "pistol-grip" arrangement in which a handle 60 of the housing 56 is configured to rest in a palm of a hand of the practitioner, and the control member 58 configured to be pivotably pulled towards or released away from the handle 60 with one or more fingers of the hand of the practitioner. Other arrangements of the actuator 50 are contemplated, for example a rotary knob disclosed in commonly owned U.S. Pat. No. 10,441,295, issued Oct. 15, 2019, the entire contents of which are hereby incorporated by reference. A frame 62 may be integrally formed with and extend distal to (or forward of) the handle 60 in a generally L-shaped arrangement. As used herein, distal or distally refers to a direction away from the practitioner, and proximal or proximally refers to a direction towards the practitioner. The housing 56 may comprise mirrored housing shells 64, 66 joined together, which may be manufactured from polymers, metals, composites, and combinations thereof. For example, each of the housing shells 64, 66 may be injection molded so as to be low cost and disposable after a single use. The housing shells 64, 66 may at least partially define an interior of the housing 56 sized and shaped to accommodate several components of the actuator 50 to be described.

Figure 7:
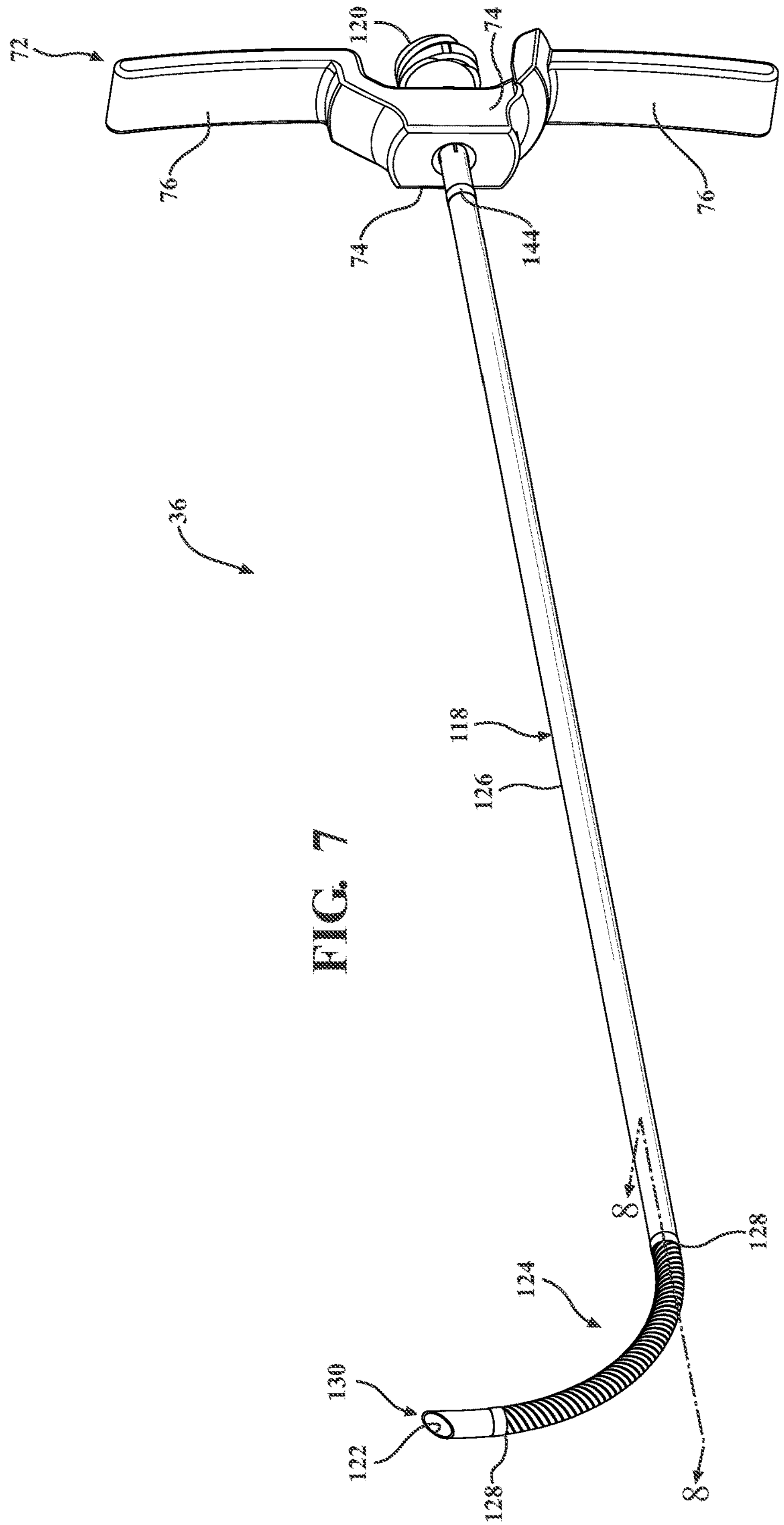
FIG. 7 is a perspective view of the sheath device with a flexible region assuming a curve.

Near its distal end, the frame 62 of the housing 56 may include shoulders 68 defining a slot 70 therebetween. One of the housing shells 64 includes one of the shoulders 68, and the other one of the housing shells 66 includes the other one of the shoulders 68 such that the shoulders 68 are generally positioned at the three and six o'clock positions. The slot 70 is oriented vertically between the shoulders 68 and sized to receive a hub 72 of the sheath device 36, as best shown in FIG. 2. More particularly, the hub 72 of the sheath device 36 includes flats 74 (see also FIG. 7) positioned adjacent a respective one of the shoulders 68 when the hub 72 is removably and slidably received within the slot 70 of the frame 62. The resulting arrangement prevents rotation of the sheath device 36 relative to the introducer device 32. As such, a hand of the practitioner is freed from separately having to maintain the rotational position of the sheath device 36 as he or she manipulates the introducer device 32 to a desired orientation. The resulting arrangement may further facilitate ease with retraction and removal of the introducer device 32 from the sheath device 36 after deployment within the vertebral body in a manner to be further explained. Still further, the resulting arrangement may prevent or twisting or kinking of the sheath device 36 as the practitioner manipulates the introducer device 32 in the constrained state against resistance of the cancellous bone in the vertebral body. The hub 72 of the sheath device 36 may further include wings 76 positioned between the flats 74 so as to be aligned with the slot 70 of the frame 62 when the hub 72 is removably and slidably received within the slot 70 of the frame 62. The wings 76 may provide not only ergonomic surfaces for one or more fingers of the physician, but also a visual indication as to a direction of curvature of the introducer device 32 once actuated to the constrained state. Further indication of the direction of curvature of the introducer device 32 once actuated to the constrained state may be provided elsewhere on the housing 56. In one implementation, indicia 78 such as a line may be positioned on a proximal side of the frame 62. The indicia 78 and an upper one of the wings 76 may function as rear and forward sights, respectively—which are already within his or her field of view over the surgical site, to provide intuitive guidance to the practitioner. Additionally or alternatively, the indicia 78 may be positioned on one or both the wings 76 of the sheath device 36. The indicia 78 may be on an upper one of the wings 76 corresponding to a direction of curvature of the flexible distal portion 82 of the sheath device 36, as generally shown in FIG. 7. Subsequent to removal of the introducer device 32 from the sheath device 36, the indicia 78 being positioned on the wings 76 provide visual indication as to the direction of curvature of the flexible distal portion 82 within the vertebral body. By extension, the indicia 78 may provide further visual indication as to the direction that subsequent components directed through the sheath device 36 may be extend from the flexible distal portion 82.

The proximal side of the frame 62 may include a flattened surface 65 (see FIG. 4) configured to receive an impact force from a surgical mallet or the like. During deployment of the introducer device 32 beyond the distal end 48 of the access cannula 34, it may be indicated to impact the flattened surface 65 with the mallet one or more times to facilitate channeling of the introducer device 32 through the cancellous bone of the vertebral body. Likewise, the impacting may facilitate channeling of the introducer device 32 through necrotic tissue or tumorous tissue that may be present within the vertebral body. The flattened surface 65 may be positioned proximal to the handle 60 to define a proximal end of the introducer device 32. The flattened surface 65 may be at least substantially planar, and further may be at least substantially circular. The circularity of the flattened surface 65 may corresponding in shape and size to a head of the mallet, thus providing an intuitive indication of the appropriate location to impact the introducer device 32 with the surgical mallet. Further, with the frame 62 and the handle 60 forming the pistol grip, the user may firmly support the handle 60 in one hand while impacting the flattened surface 65 of the frame 60 with the mallet being held in the other hand.

The shaft 52 of the introducer device 32 includes a rigid proximal portion 80 and the flexible distal portion 82. Referring now to FIGS. 3 and 4, the proximal portion 80 of the shaft 52 extends through a bore of the frame 62 to a position within the interior of the handle 60. The proximal portion 80 of the shaft 52 may be axially and rotationally fixed relative to the actuator 50. A retaining block 85 may be disposed within the interior of the handle 60 with a proximal end of the proximal portion 80 of the shaft 52 being secured to the retaining block 85. The proximal portion 80 may be formed from rigid material(s) with sufficient mechanical properties to avoid more than minimal flexure.

Figure 5B:
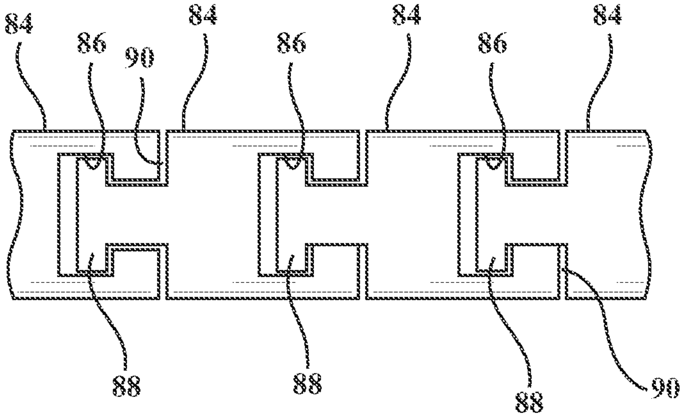
FIG. 5B is a sectional view of the portion of the shaft within detail 5B-5B.
Figure 5A:
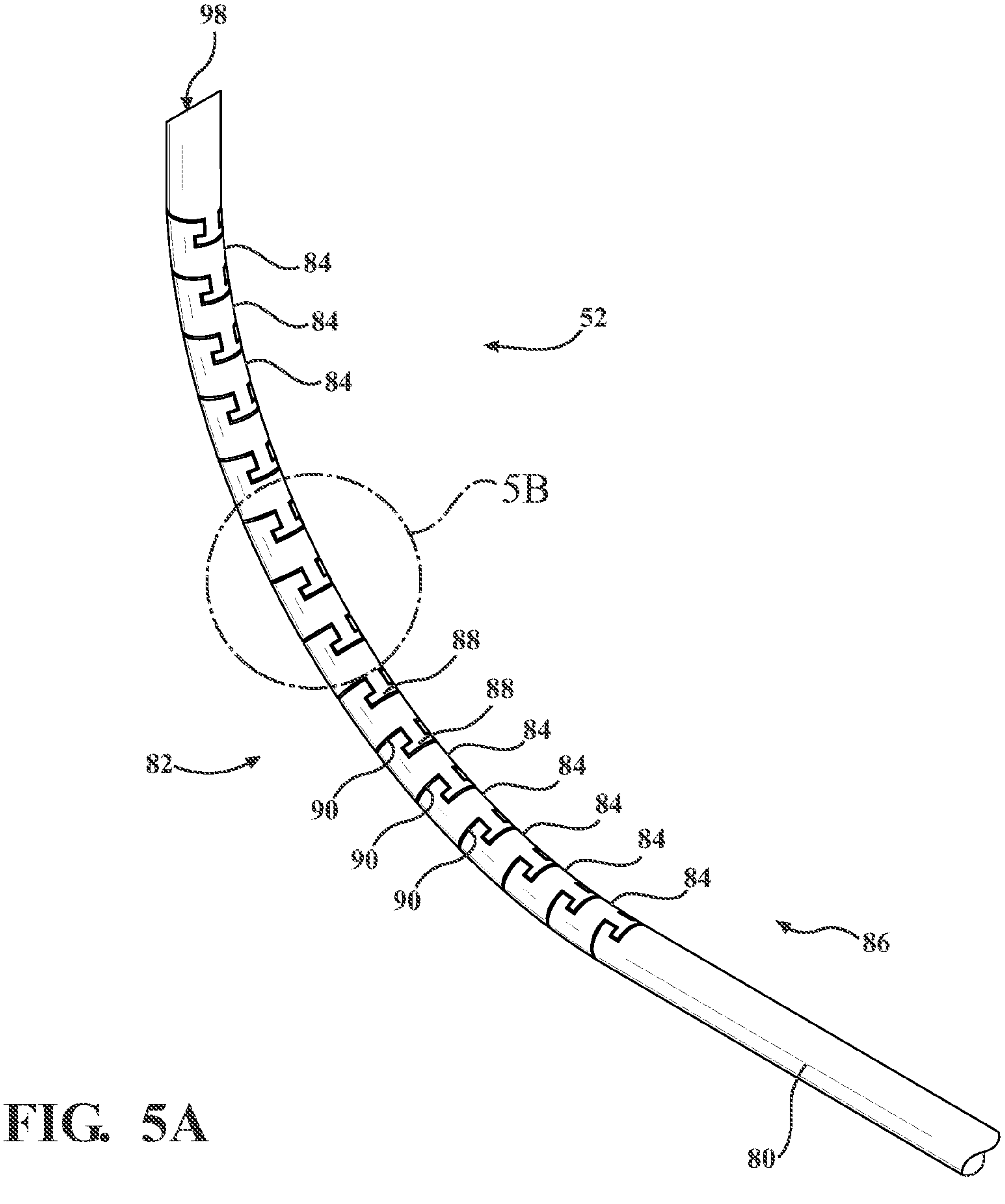
FIG. 5A is a perspective view of a portion of the shaft of the introducer device.
Figure 6:
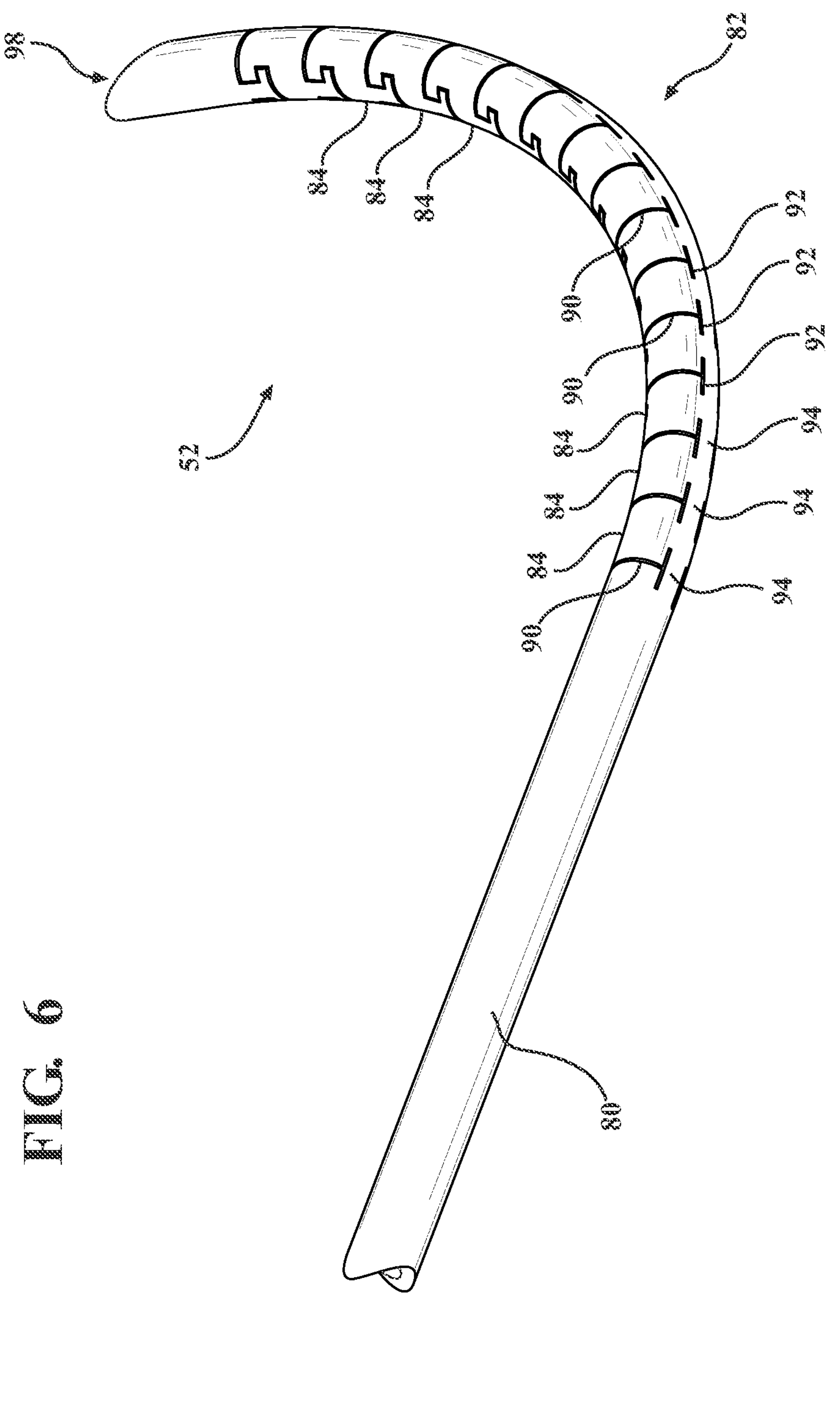
FIG. 6 is another perspective view of the shaft of the introducer device in the constrained state.

The distal portion 82 extends from the proximal portion 80. With further reference to FIGS. 5A and 6, a transition between the proximal portion 80 and the distal portion 82 may be defined by a first of a series of geometries within the shaft 52. The series of geometries may provide a series of interconnected segments 84. The interconnected segments 84 may be of unitary construction. In other words, the segments 84 may not be discrete links, but rather subportions of the distal portion 82 configured to articulate relative to one another. As a result, the shaft 52 including the proximal and distal portions 80, 82 may comprise or be formed from a single piece of metal. In one implementation, the geometries may be laser cut into the single piece of metal. More particularly, the geometries may take the form of slots 86 defined within an upper side of the distal portion 82. The slots 86 may be T-shaped as shown in FIG. 5B. The geometries may further include protrusions 88 corresponding to the shape of the slots 86. The protrusions 88 may also be T-shaped. With the introducer device 32 in the unconstrained state and the distal portion 82 generally straight, gaps are between the protrusions 88 and an adjacent edge of the slots 86. As the introducer device 32 is moved to the constrained state, the gaps between the protrusions 88 and the adjacent edges of the slots 86 are closed. Further tension provided by a pulling element 54 with the contact of the adjacent segments 84 provides rigidity to the distal portion 82. The tension is sufficient for the introducer device 32 to assume and/or maintain a curve within the vertebral body with advancement of the distal portion 82 beyond the distal end 48 of the access cannula 34.

The slots 86 and protrusions 88 may be disposed on an upper or concave side of the distal portion 82, as generally appreciated from FIG. 5A. With further reference to FIG. 6, extending from the slots 86 are first slits 90, and the first slits 90 extend about a portion of the outer diameter of the distal portion 82. The first slits 90 may be oriented transverse to the longitudinal axis. The first slits 90 of the illustrated implementation extend about a majority of the outer diameter. Further geometries may be disposed on a lower or convex side of the distal portion 82, and those geometries may interconnect the segments 84. More specifically, the first slits 90 terminate at second slits 92 to define spine sections 94 between opposing pairs of the second slits 92. The second slits 92 may be angled relative to the first slits 90, for example, at right angles such that the second slits 92 are oriented parallel to the longitudinal axis of the distal portion 82. Owing to the flexibility of the material forming the distal portion 82, the spine sections 94 are configured to flex. The flexure of the spine sections 94 is at least sufficient to permit the protrusions 88 to move within the slots 86 into contact with the adjacent edges as previously described. The resulting arrangement provides for relative movement of the segments 84 and, in the aggregate, articulation of the distal portion 82 over its length. The extent of articulation or curvature of the distal portion 82 may be selectively controlled through selective tensioning of the pulling element 54. The angle of articulation or curvature may be designed within the range of approximately 50 to 150 degrees, and more particularly within the range of approximately 65 to 125 degrees, and even more particularly within the range of approximately 80 to 100 degrees. FIGS. 4, 5A and 6 show the distal portion 82 oriented at an angle of approximately 90 degrees relative to the proximal portion 80. In alternative implementations, the reverse configuration is contemplated in which the slots 86 and protrusions 88 may be disposed on the lower or concave side of the distal portion 82, and the first and second slits 90, 92 are disposed on the upper or concave side of the distal portion 82.

It is contemplated that the user may rotate the introducer device 32 during or after deployment of the distal portion 82 within the vertebral body in order to steer the distal portion 82 to a target location. Owing to the presence of cancellous bone within the vertebral body, the distal portion 82 including the segments 84 endure torqueing as the introducer device 32 is rotated. The segments 84 of the distal portion 82 may advantageously be designed to achieve the desired steerability while providing compliance or flexibility of the segments 84 to handle the torque. In certain implementations, lateral aspects of the slots 86 and/or lateral aspects of the protrusions 88 (see FIG. 5B) may be sized to define a gap of a specific size such that adjacent segments 84 may be free to rotate slightly relative to one another prior to the complementary lateral aspects engage one another. The "rotational play" between the adjacent segments 84 may limit torqueing on the segments 84 during initial rotation of the introducer device 32. Once the complementary lateral aspects engage one another, the segments 84 become rigid in nature and preserve steerability with subsequent rotation of the introducer device 32.

With the introducer device 32 being rotated in the constrained state, it should be appreciated that more proximal segments 84 endure more torque than more distal segments 84. For example, the counteracting forces from the cancellous bone on a distal end 98 of the shaft 52 result in heightened torque on a proximal-most one of the segments 84 (i.e., adjacent the proximal portion 80) with further rotation of the introducer device 32. The introducer device 32 of the present disclosure advantageously contemplates varying the design of individual segments 84 to account for the gradient of anticipated torque along a length of the distal portion 82. In one implementation, the aforementioned gaps between the complementary lateral aspects of the slots 86 and the protrusions 88 may decrease more distally along a length of the distal portion 82. The arrangement results in more distal adjacent segments 84 being more rigid in function relative to more proximal adjacent segments 84 during rotation of the introducer device 32. In another implementation and with reference to FIG. 6, the spine sections 94 may be of varying widths along the length of the distal portion 82. More particularly, the width of the spine sections 94 may progressively decrease distally along the length of the distal portion 82 such that the spine sections 94 of the proximal-most segments 84 are wider to endure greater torque. The reverse configurations of the gaps and/or the spine sections 94 are contemplated as well.

Referring again to FIGS. 3 and 4, the pulling element 54 is coupled to the actuator 50 and the shaft 52, and more particularly the distal portion 82 of the shaft 52. The pulling element 54 includes a proximal end coupled to the control member 58 of the actuator 50. The pulling element 54 may be secured to the control member 58 with an interference connector 96, for example a ferrule, nut, swaged sleeve, clamp, or other suitable connector. The connector 96 may be sized to movably ride within a slot defined by complementary pockets in each of the housing shells 64, 66. An input to the control member 58 (e.g., pulled towards the handle 60) urges the connector 96 proximally within the slot, thereby tensioning the pulling element 54.

The pulling element 54 includes a distal end coupled to the shaft 52 at or near its distal end 98. The pulling element 54 extends through a lumen 100 of the shaft 52, and may be joined at or near the distal end 98 of the shaft 52 through brazing, welding, adhesive, interference fit, or other suitable joining process. The distal end of the pulling element 54 may be coterminous with the distal end 98 of the shaft 52. The pulling element 54 may be monolithic in construction and comprise or be formed from a metal, polymer, composite, or combination thereof. For example, the pulling element 54 may be a wire rope, a wire, a rod, and the like, of solid or hollow construction.

In certain implementations, the pulling element 54 may be coupled to the shaft 52 with a hypotube (not shown). The hypotube may have an inner diameter slightly greater than an outer diameter of the pulling element 54, and an outer diameter slightly less than an inner diameter of the shaft 52. The hypotube may have a length sized to be disposed within a distalmost of the interconnected segments 84. In one example, the hypotube has a length of approximately three millimeters. The hypotube may be secured over a distal end of the pulling element 54, for example, by crimping. The outer surface of the hypotube may then be welded or otherwise secured to the inner surface of the shaft 52. The hypotube being crimped onto the pulling element 54 may preserve the tensile strength of the pulling element 54 relative to implementations where welding may anneal the pulling element 54 with corresponding reduction in tensile strength.

As previously mentioned, the pulling element 54 is configured to be selectively tensioned to alter the extent of the articulation or curvature of the distal portion 82. With the introducer device 32 in the unconstrained state (see FIG. 3), minimal or zero tension may be exerted on the pulling element 54, also referred to herein as a first tension. It should be appreciated that some minimal tension may be on the pulling element 54 in the unconstrained state. The input to the control member 58 increases the tension on the pulling element 54 to move the introducer device 32 to the constrained state, also referred to herein as a second tension. The second tension is greater than the first tension.

The actuator 50 may be locked with the introducer device 32 in the constrained state. The actuator 50 may include a locking mechanism 102 for operably coupling the housing 56 and the control member 58 and configured to permit selective locking of the control member 58. The locking mechanism 102 of the implementation shown in FIGS. 3 and 4 provides for simplified, cost-effective construction and intuitive operation. Each of the shells 64, 66 includes the handle 60 defines a proximal opening 104 and includes a ramp 106 and a retention feature 108 adjacent the ramp 106. The ramp 106 and the retention feature 108 may define an upper portion of the proximal opening 104, and the proximal opening 104 may be ergonomically positioned on the handle 60 to be easily accessible by the thumb of the practitioner when holding the actuator 50 of the introducer device 32 (see FIG. 2). The locking mechanism 102 may further include an arm 110 coupled to and extending from the control member 58 in a direction opposite the control surface 59. FIGS. 3 and 4 show the arm 110 extending proximally from the control member 58 towards the handle 60. A lock head 112 is at the end of the arm 110. The arm 110 and lock head 112 are arranged and dimensioned such that, as the control member 58 is pivoted towards the handle 60 as the actuator 50 is actuated, the lock head 112 moves towards and assumes a position within the proximal opening 104.

The lock head 112 is configured to releasably engage the retention feature 108 of the handle 60. The arm 110 is resilient and configured to deflect as the lock head 112 moves along the ramp 106 of the handle 60. More particularly, as the control member 58 is pivoted towards the handle 60, an upper surface of the lock head 112 contacts the ramp 106. The interference between the lock head 112 and the ramp 106 results in the arm 110 deflecting downwardly with further pivoting of the control member 58 with force sufficient to overcome the interference. A notch 114 on the lock head 112 moves past the ramp 106, and the dimensions of the notch 114 permit the arm 110 to resiliently return to an original state in which the notch 114 engages the retention feature 108, as shown in FIG. 4. The resilient return of the arm 110 is sudden, and the lock head 112 contacting the retention feature 108 may result in an audible and/or tactile feedback to the practitioner. Particularly when the actuator 50, including the control member 58, the handle 60, the arm 110, and the lock head 112 are formed from plastic, the plastic-on-plastic impact may make a sound audible to the practitioner. Along those lines, the locking mechanism 102 of the present disclosure provides for a low-cost design that is more easily manufacturable than, for example, a ratchet mechanism. It should be understood that the other suitable mechanism for selectively locking the introducer device 32 in the constrained state are contemplated. One suitable example is described in the commonly-owned U.S. Pat. No. 9,839,443, hereby incorporated by reference in its entirety, in which a ratchet is configured to be selectively locked one of a plurality of positions corresponding to different tensions on the pulling element and different angles of curvature of the steering instrument.

With the locking mechanism 102 locked, the tension of the pulling element 54 is maintained, and thus the introducer device 32 is maintained in the constrained state. As mentioned, the lock head 112 extends through the proximal opening 104. The lock head 112 includes a release surface 116 positioned proximal to the proximal opening 104 so as to be engageable by the thumb of the practitioner. In manners to be described, once the introducer device 32 is actuated and positioned within the vertebral body, the workflow includes the step of removing the introducer device 32 from the sheath device 36. The introducer device 32 should be moved to the unconstrained state to do so, otherwise the curvature of the distal portion 82—having rigidity from the tension of the pulling element 54 are previously explained—would prevent the practitioner from removing the introducer device 32 from the sheath device 36. In an ergonomic and intuitive step, the practitioner may simply engage the release surface 116 and urge the lock head 112, against the bias of the arm 110, out of engagement with the retention feature 108. The residual tension on the pulling element 54 may urge the control member 58 distally, and the introducer device 32 assumes the unconstrained state. The lock head 112 may no longer be within the proximal opening 104, providing a visual indication of the practitioner that the locking mechanism 102 has been disengaged and the introducer device 32 is in the unconstrained state.

As previously mentioned, the introducer device 32 may be operably coupled to the sheath device 36 when deployed into the vertebral body, and the workflow may include the step of removing the introducer device 32 from the sheath device 36. Subsequently, components of the system 30 may be deployed through the sheath device 36. Referring now to FIG. 7, the sheath device 36 includes the hub 72, and a sheath 118 extending from the hub 72. The hub 72 may include a fitting 120 in communication with a lumen 122 of the sheath 118 and configured to be removably coupled with another component of the system 30. One exemplary fitting is a Luer fitting.

At least a region of the sheath 118 is flexible and configured to conform to the shaft 52, and more particularly to the distal portion 82 of the shaft 52 as the introducer device 32 moved from the constrained state to the unconstrained state. With concurrent reference to FIG. 8, the flexible region 124 extends from a proximal portion 126 of the sheath 118. The proximal portion 126 is coupled to and extends distally from the hub 72, and the proximal portion 126 may be flexible or rigid. In the illustrated implementation, the proximal portion 126 is rigid and comprise or be formed from biocompatible materials with sufficient mechanical properties to maintain integrity as the sheath device 36 is retracted and advanced in a manner to be described. One exemplary material is stainless steel. The flexible region 124 may be coupled to or integrally formed with the proximal portion 126. In one example, the flexible region 124 may be a separate component joined with the proximal portion 126 at a lap joint. The flexibility of the flexible region 124 may be due to a helical pattern extending between opposing ends 128 of the flexible region 124. The helical pattern may be formed by laser cutting or other suitable manufacturing process, and it is to be understood that a helix is one exemplary geometry.

Figure 8:
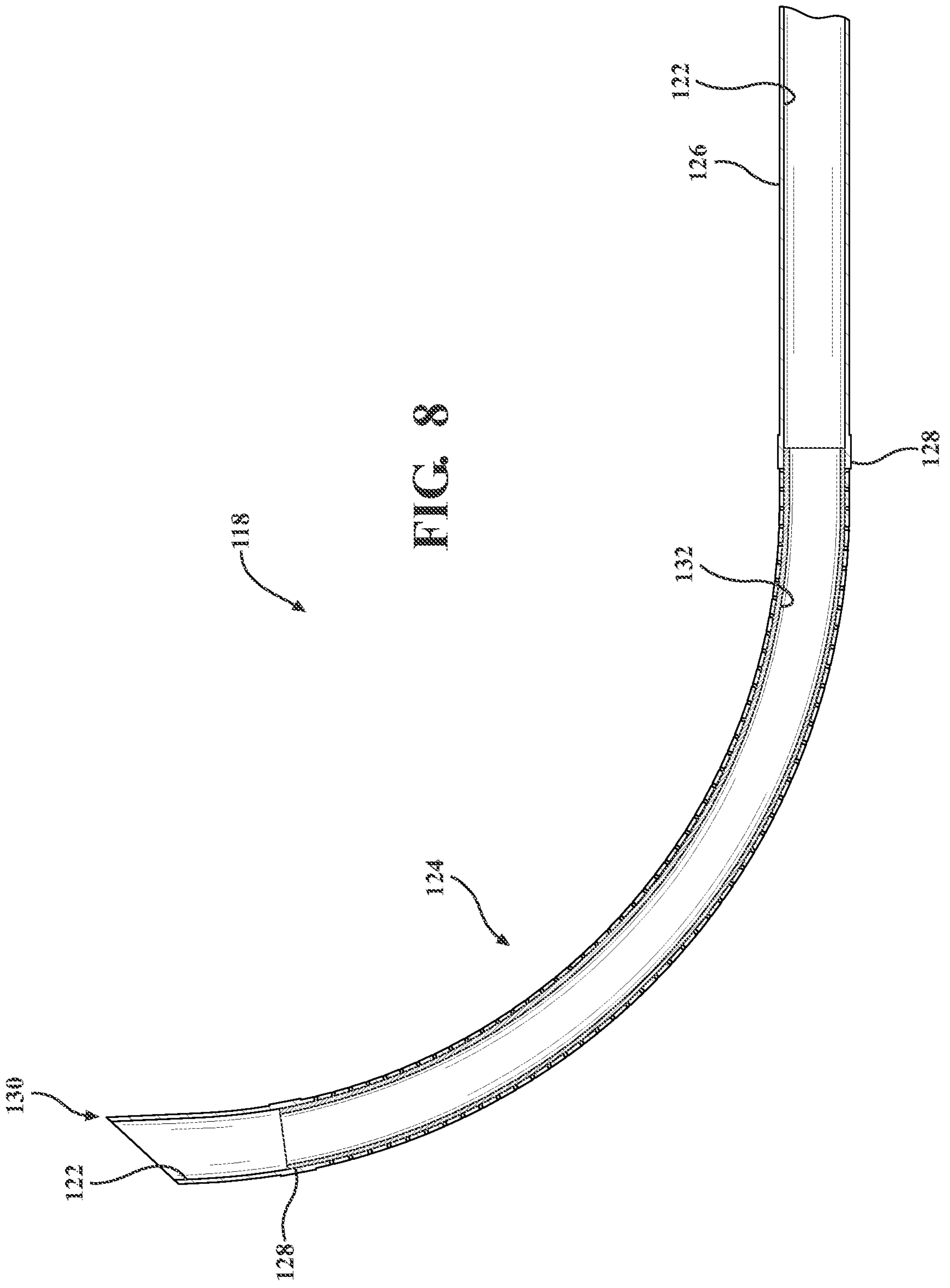
FIG. 8 is a sectional view of a portion of the sheath of FIG. 7 taken along section lines 8-8. An optional sleeve is disposed within the flexible region.

Each of the flexible region 124 and the proximal portion 126 defines a portion of the lumen 122. With the shaft 52 of the introducer device 32 disposed within the lumen 122 of the sheath 118 of the sheath device 36, the flexible region 124 of the sheath 118 is axially aligned with the distal portion 82 of the shaft 52. As a result, providing an input to the actuator 50 to move the introducer device 32 from the unconstrained state to the constrained state, the flexible region 124 of the sheath 118 assumes a curve corresponding to the articulation or curvature of the distal portion 82 of the shaft 52. As the flexible region 124 of the sheath 118 assumes the curve within the vertebral body, portions of the helical pattern may become spaced apart. In other words, small gaps may become present on the convex side of the helical pattern. As to be described, however, curable material—which is initially flowable—is to be directed through the sheath 118 of the sheath device 36. It may not be desirable for egress of the curable material through the small gaps, as the target location is generally considered to be at a distal end 130 of the sheath 118. Stated differently, it is generally desirable for the curable material to be directed through and out of the lumen 122 at the distal end 130 of the sheath 118. The sheath 118 of the present disclosure advantageously prevents such egress by including a sleeve 132 coaxially disposed within or exterior to the flexible region 124 of the sheath 118. As best shown in FIG. 8, the sleeve 132 is coupled to the sheath 118 at or near the opposing ends 128 of the flexible region 124. The sleeve 132 is polymeric so as to have the necessary elasticity and flexibility to traverse the curve assumed by the flexible region 124. Whereas FIG. 8 shows the sleeve 132 disposed within the flexible region 124, a reverse configuration is contemplated in which the sleeve 132 is disposed on an exterior of the flexible region 124. In operation, the curable material being directed through the sheath 118 encounters the sleeve 132 so as to traverse the curve to be directed through the lumen 122 at the distal end 130 of the sheath 118.

In certain implementations, the sleeve 132 may be preformed with a curve. The preformed curve may facilitate the flexible region 124 to curve when the introducer device 32 is removed from the sheath device 36. Additionally or alternatively, the flexible region 124 of the sheath 118 may be preformed with a curve. The preformed curve may also facilitate the flexible region 124 to curve when the introducer device 32 is removed from the sheath device 36. For example, the flexible region 124 may be metal, and the preformed curve may be plastically deformed during manufacturing of the sheath 118. For another example, the preformed curve of the metal may be facilitated with the geometries such as the helix. The preformed curve of the flexible region 124 and/or the sleeve 132 may be designed with a curvature within the range of approximately 50 to 150 degrees, and more particularly within the range of approximately 65 to 125 degrees, and even more particularly within the range of approximately 80 to 100 degrees. In one implementation, the preformed curve may be approximately 90 degrees. The preformed curve may advantageously facilitate the sheath 118 traversing the curved path within the cancellous bone during advance of the sheath 118 with the introducer device 32. The curved path may be created with more reproducibility, as there is less reliance on the introducer device 32 in the constrained state. In other words, the introducer device 32 and the sheath device 36 cooperate by each providing a portion of the lateral forces to impart the curve within the cancellous bone. Additionally, the preformed curve may advantageously facilitate the sheath 118 traversing the curved path within the cancellous bone during advance of the sheath 118 without the introducer device 32. For example, after deployment and removal of the cavity-forming device 160 and prior to the deployment of curable material to within the cavity, it may be desirable to advance of the sheath 118 to a distal margin of the cavity. The preformed curve may avoid the distal end 130 of the sheath 118 "bottoming out" or snagging the convex side of the curved path and/or the cavity.

Figure 11A:
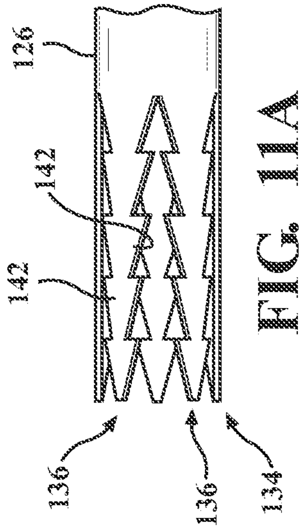
FIG. 11A is another implementation of the protrusions.
Figure 11B:
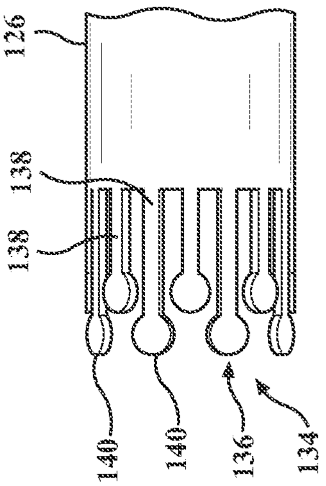
FIG. 11B is another implementation of the protrusions.
Figure 11C:
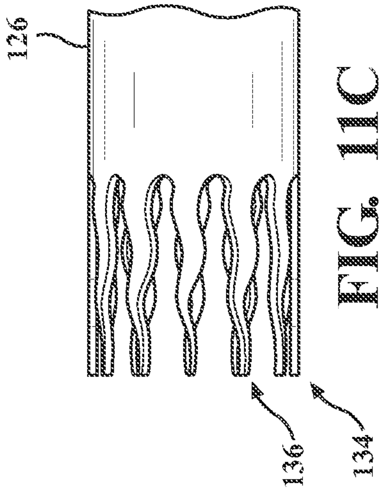
FIG. 11C is another implementation of the protrusions.
Figure 9:
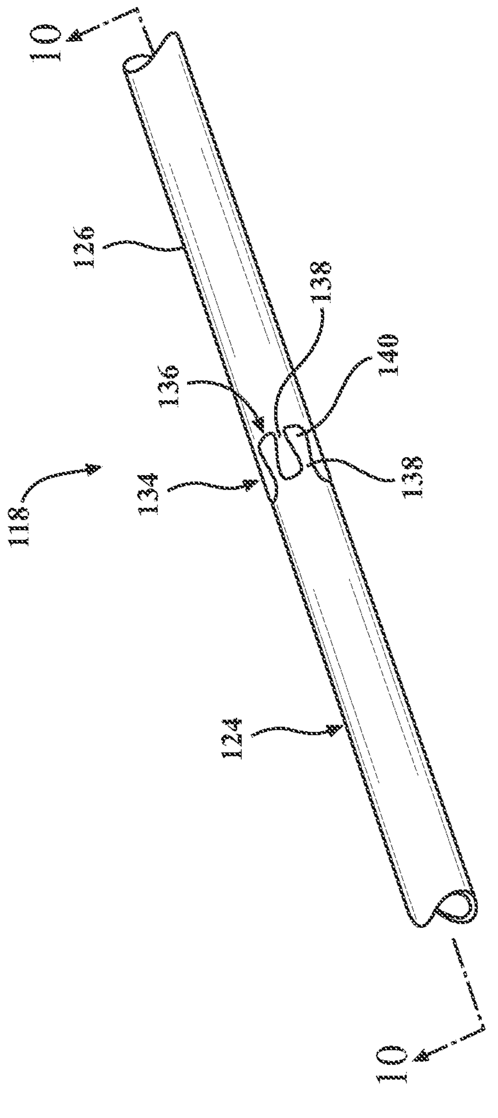
FIG. 9 is a perspective view of a portion of the sheath including protrusions defining an interface between a polymeric region and a proximal portion.
Figure 10:
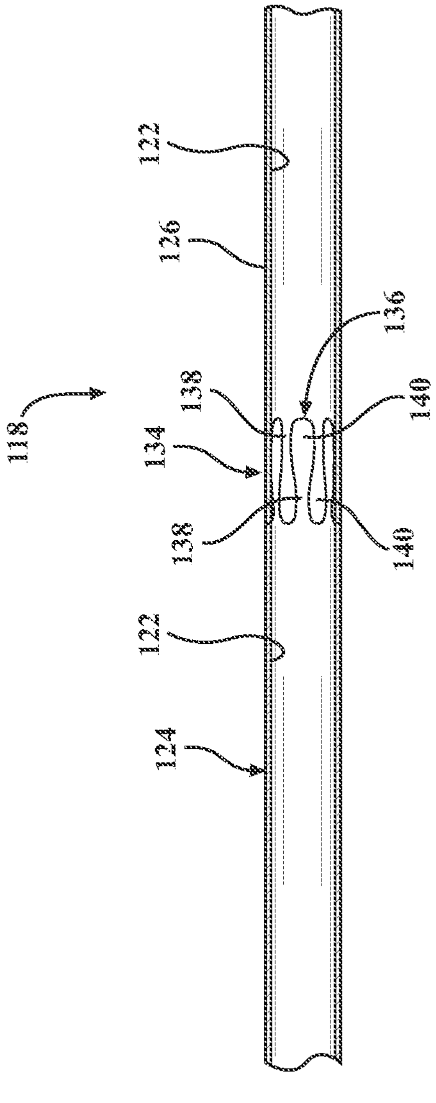
FIG. 10 is a sectional view of the portion of the sheath of FIG. 9 taken along section lines 10-10.

Referring now to FIGS. 9-11C, the flexible region 124 may comprise or be formed from a flexible biocompatible polymer having sufficient hoop strength to patent upon removal of the introducer device 32 from the sheath 118. Suitable flexible polymers include polypropylene, polyether ether ketone (PEEK), and the like. More particularly, the polymeric region 124 is coupled to the proximal portion 126 at an interface 134 having protrusions 136 resulting in a constant contour of the lumen 122 (i.e., the inner diameter), as best shown in FIG. 10, and a constant outer diameter. The protrusions 136 include complementary fingers or tines configured to be joined to one another. An adhesive or other joining process may also be utilized to strengthen the interface 134. The protrusions 136 may be radially disposed about the polymeric region 124 and the proximal portion 126. The protrusions 136 may be further disposed equiangularly about the longitudinal axis. FIGS. 9 and 10 show each of the protrusions having a neck 138, and a head 140 larger than the neck 138. The neck 138 may be a thinned region widening into a bulbous or circular profile defining the head 140. The head 140 engaging the neck 138 of an adjacent one of the fingers 136 provides an axial retention force. Alternative implementations are shown in FIGS. 11A-11C. FIG. 11A shows each side of the tines 136 including serrations 142 to provide a barb. FIG. 11B shows every other neck 138 is longer so that the heads 140 are axially staggered. FIG. 11C shows the tines being wavy in shape and tapering to a point.

In another implementation, an entirety of the sheath 118 may comprise or be formed from a flexible biocompatible polymer having sufficient hoop strength to patent upon removal of the introducer device 32 from the sheath 118. In other words, from distal to the hub 72 to the distal end 130, the sheath 118 may be polymeric. Suitable flexible polymers include polypropylene, polyether ether ketone (PEEK), and the like. The implementation of the sheath 118 formed entirely from the flexible biocompatible polymer may also include a preformed curve. A heat-based process may impart the preformed curve in the polymer. The preformed curve may facilitate the flexible region 124 to curve when the introducer device 32 is removed from the sheath device 36. Additionally or alternatively, the flexible region 124 of the sheath 118 may be preformed with a curve. The preformed curve may also facilitate the flexible region 124 to curve when the introducer device 32 is removed from the sheath device 36. The preformed curve may be a curvature within the range of approximately 50 to 150 degrees, and more particularly within the range of approximately 65 to 125 degrees, and even more particularly within the range of approximately 80 to 100 degrees. In one implementation, the preformed curve may be approximately 90 degrees. Further, the polymer sheath 118 may include a reinforcement, such as braiding and/or coiling, with metal or other polymers. The polymer sheath 118 being of unitary construction may provide simplified design and/or reduced manufacturing costs. Still further, the polymer sheath 118 may be filled with a radiopaque material, such as barium or tungsten. With polymers being less visible on fluoroscopy, and the entirety of the sheath 118 being a polymer, the radiopaque material may be particularly well suited to facilitate real-time visual guidance with fluoroscopy subsequent to removal of the introducer device 32 from the sheath device 36.

A workflow of performing a vertebral augmentation with the system 30 will now be described with particular reference to FIGS. 12, 13, 15, 16, 19, 20 and 21. The vertebra with the offending vertebral body may be confirmed on fluoroscopic imaging. An incision may be made in the overlying paraspinal musculature lateral of midline generally in alignment with one of the pedicles of the vertebra. The distal end 48 of the access cannula 34, with the trocar disposed therein, is directed through the pedicle a position beyond the cortical rim and within the interior region of the vertebral body, and the trocar is removed. The access cannula 34 provides the working channel to within the interior region of the vertebral body along the longitudinal axis. The cannula hub 42 is exposed and configured to be engaged by the introducer device 32.

Figure 12:
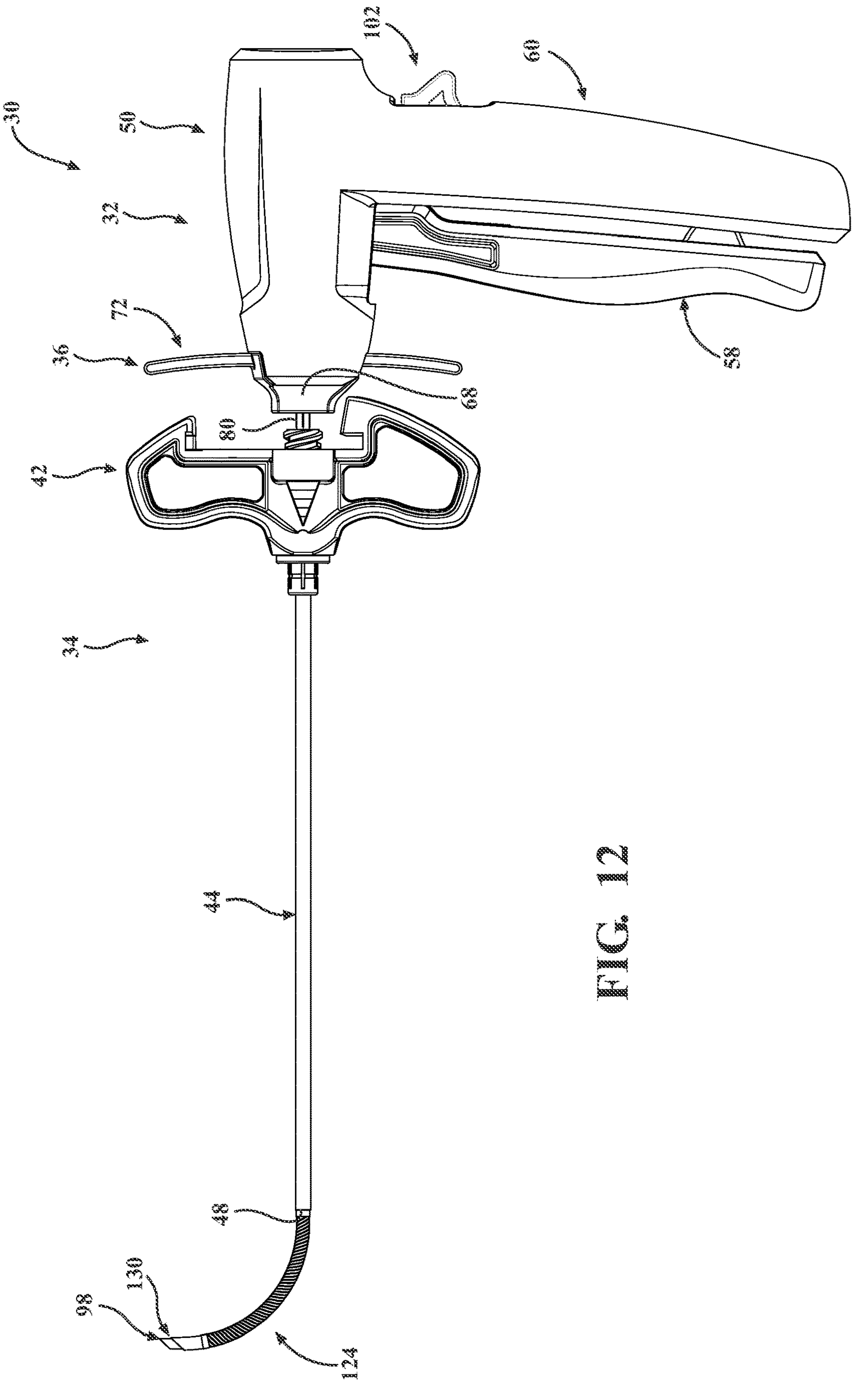
FIG. 12 is an elevation view of the system with the introducer device in the constrained state and the flexible region of the sheath assuming the curve.
Figure 13:
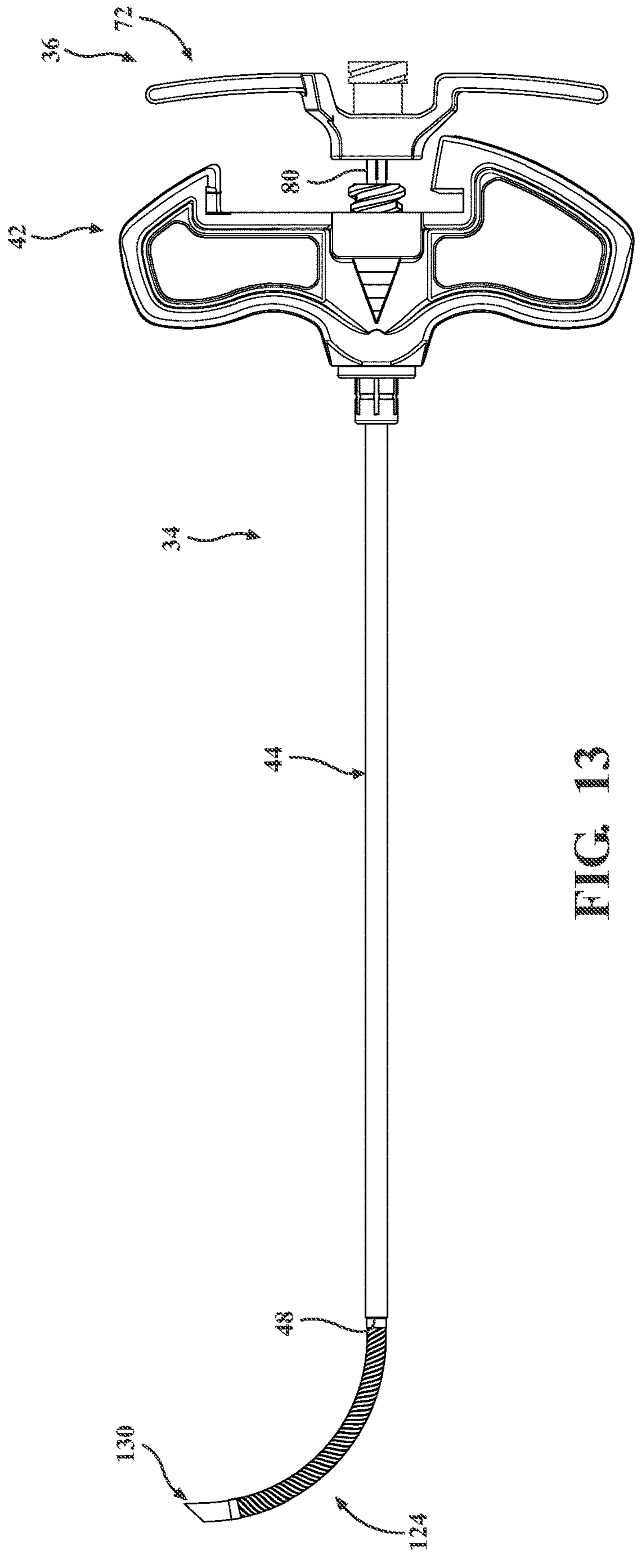
FIG. 13 is an elevation view of the system subsequent to removal of the introducer device from the sheath device in which the flexible region of the sheath remains curved beyond the distal end of the access cannula.

The shaft 52 of the introducer device 32 has a length sufficient to extend through and be operable beyond the distal end 48 of the access cannula 34. Likewise, the sheath 118 of the sheath device 36 has a length sufficient to extend through and be operable beyond the distal end 48 of the access cannula 34, and the length of the shaft 52 may further extend through the distal end 130 of the sheath 118. FIG. 12 shows the distal end 98 of the shaft 52 being slightly distal to the distal end 130 of the sheath 118. Each of the distal ends 98, 130 may include a reverse bevel to facilitate penetration of the cancellous bone during deployment of the system 30. The bevel may be fabricated through electrochemical grind, electrical discharge machining (EDM), or other suitable manufacturing process. With the introducer device 32 operably coupled to the sheath device 36 and the components positioned near in operable engagement with the cannula hub 42 of the access cannula 34, as shown in FIG. 12, the distal portion 82 of the introducer device 32 and the flexible region 124 of the sheath 118 is configured beyond the distal end 48 of the cannula shaft 44.

The workflow includes directing the shaft of the introducer device 32 and the sheath 118 to within the access cannula 34 such that the distal portion 82 of the introducer device 32. The introducer device 32 is in the unconstrained state in which the pulling element 54 is at the first tension that is zero or near zero. Furthermore, the flexible region 124 of the sheath 118 remains within the access cannula 34. In other words, the distal ends 98, 130 of the shaft 52 and the sheath 118 are positioned proximal to or in registration with the distal end 48 of the access cannula 34. This may be facilitated with indicia 144 disposed on the sheath 118 (see FIG. 7). The indicia 144 may be aligned with the hub 42 of the access cannula 34 such that, when the indicia 144 is in alignment with a proximal end of the cannula hub 42, the distal end 130 of the sheath 118 is in registration with the distal end 48 of the access cannula 34. Thereafter, an input is provided to the actuator 50 to move the introducer device 32, for example, pivoting the control member 58 towards the handle 60. The pivoting of the control member 58 to which the pulling element 54 is coupled, moves the introducer device 32 from the unconstrained state to the constrained state in which the pulling element 54 is at the second tension greater than the first tension. As previously described, this would otherwise result in the distal portion 82 of the introducer device 32 being articulated and the flexible region 124 of the sheath 118 assuming a curve from the longitudinal axis; however, the access cannula 34 prevents the distal portion 82 of the shaft 52 and the flexible region 124 of the sheath 118 from doing so. An appreciable amount of potential energy is stored in the pulling element 54 at the second tension.

The physical characteristics of the pulling element 54 (e.g., modulus of elasticity) is such that the locking mechanism 102 of the introducer device 32 may be actuated to the locked state despite the cannula shaft 44 constraining the distal portion 82 of the shaft 52 and the flexible region 124 of the sheath 118 from assuming the curve. As previously described, the arm 110 of the locking mechanism 102 flexes until the lock head 112 passes the ramp 106, and resiliently returns to provide interface engagement between the notch 114 and the retention feature 108. An audible and/or tactile indication may be provided to the practitioner that the introducer device 32 is locked in the constrained state. The lock head 112 is positioned thorough the proximal opening 104 as shown in FIG. 12.

Prior to or after moving the introducer device 32 from the unconstrained state to the constrained state, the introducer device 32 and the sheath device 36 may be rotated relative to the access cannula 34 onto a desired, anticipated plane of curvature (once advanced within the vertebral body). The handle 60 may be rotated, and owing to the engagement of the flats 74 of the hub 72 and the shoulders 68 of the frame 62, the sheath device 36 is correspondingly rotated. The desired plane of curvature may be provided by the indicia 78 on the proximal side of the frame 62 and/or the wings 76 of the hub 72.

Thereafter, the introducer device 32 and the sheath device 36 are advanced relative to the access cannula 34 with the introducer device 32 in the constrained state. The distal portion 82 of the shaft 52 and the flexible region 124 of the sheath 118 are moved distally beyond the distal end 48 of the access cannula 34 to within the vertebral body. The pulling element 54 is at the second tension and, as the distal portion 82 of the shaft 52 and the flexible region 124 of the sheath 118 are moved beyond the distal end 48 of the access cannula 34, the stored potential energy causes the distal portion 82 of the shaft 52 to articulate or curve. The flexible region 124 of the sheath 118 correspondingly assumes the curve. The advancement may be characterized the components plunging through cancellous bone of the vertebral body while simultaneously assuming the curve. The result is shown in FIG. 12. The distal ends 98, 130 of the shaft 52 and the sheath 118 are positioned at the target site offset from the longitudinal axis.

Thereafter, it is indicated to remove introducer device 32 from the sheath device 36 with the distal end 130 of the sheath 118 remaining positioned at the target site offset from the longitudinal axis. The lumen 122 of the sheath 118 provides a pathway to the target site to locations within the vertebral body with the pathway facilitating the remaining steps of the vertebral augmentation procedure. Owing to the tension on the pulling element 54 and the slot 86 and protrusion 88 engagement, the distal portion 82 of the shaft 52 has rigidity that prevents removal of the shaft 52 from the sheath 118. Therefore, it may be indicated to lessen or remove the tension from the pulling element 54. The locking mechanism 102 is actuated from the locked state to the unlocked state. In particular, an input is provided to the release surface 116 to disengage the lock head 112 from the retention feature 108, and the pulling element 54 at least substantially returns to the first tension. Owing to the presence of cancellous bone within which the distal portion 82 of the shaft 52 and the flexible region 124 of the sheath 118 have assumed a curve, moving the locking mechanism 102 to the unlocked state may not result in the distal portion 82 of the shaft 52 and the flexible region 124 of the sheath 118 returning to a straight. The introducer device 32, however, moves from the constrained state to the unconstrained state, whereby pulling element 54 being at the first tension provides for removal of the introducer device 32 from the sheath device 36 with the flexible region 124 of the sheath 118 remaining curved within the vertebral body. The result in shown in FIG. 13.

The position of the distal end 130 of the sheath 118 may be confirmed via fluoroscopy. The sheath 118 being metal may be visible on fluoroscopy, and in implementations using the polymer region, one exemplary manner to confirm the position includes radiopaque markers as disclosed in commonly owned United States Patent Publication No. 2020/0383707, published Dec. 10, 2020, the entire contents of which are hereby incorporated by reference. Should the position of the distal end 130 be suboptimal prior to removal of the introducer device 32 from the sheath device 36, the system 30 advantageously facilitates repositioning of the sheath device 36 without requiring the sheath device 36 be removed from the access cannula 34 to be redeployed. Existing systems may require removal of the sheath device 36, which may undesirably increase the likelihood of material degradation of the sheath 118. For example, in cases where a sheath is formed only from a polymer such as PEEK, there may be pronounced frictional forces on the sheath from the distal end 48 of the access cannula 34 as it is being removed. With the system 30 including the introducer device 32, the practitioner may provide another input to the actuator 50 to increase the tension the pulling element 54 while the distal portion 82 of the shaft 52 and the flexible region 124 of the sheath device 36 are within the interior region of the vertebral body. The practitioner may manipulate the handle 60 as desired, then return the introducer device 32 to the unconstrained state at a second or subsequent target site that is offset from the longitudinal axis. It is understood that any number of subsequent inputs may be provided to the control member 58, and multiple inputs may be provided for creating a cavity of a desired shape within the interior region of the vertebral body.

In certain implementations, it may be desirable to reposition the sheath 118 after removal of the introducer device 32 from the sheath 118. With the introducer device 32 in the unconstrained state, the shaft 52 may be redirected through the sheath 118 that is already positioned within the vertebral body. Once the introducer device 32 is deployed, the input(s) may be provided to and removed from the control member 58 of the actuator 50 to tension the pulling element 54 and reposition the sheath 118 at the second or subsequent target site. The shaft 52 of the introducer device 32 may again be removed from the sheath 118 with the sheath 118 remaining positioned at the second or subsequent target site offset from the longitudinal axis.

With the introducer device 32 removed from the sheath device 36 and with the distal end 130 of the sheath 118 remaining positioned at the target site offset from the longitudinal axis, the treatment device may be deployed through the sheath device 36. The treatment device may be a cavity-forming device 160 configured to displace tissue as part of a kyphoplasty procedure. Additionally or alternatively, the treatment device may be an electrode probe 200 device configured to ablate tissue. Other vertebral augmentation components are contemplated, for example, a drill device and/or a tissue biopsy device. The treatment device is directed through the sheath device 36 and near or in registration with the distal end 130 of the sheath 118, after which the sheath 118 is retracted relative to the component to expose the component at the target location. In order to facilitate the retraction of the sheath 118 in an ergonomic and intuitive manner, the system 30 includes the spacer lock 40. Referring now to FIGS. 14-17, the spacer lock 40 includes legs 146 extending from a hub 148 and defining at least one slot 150. The illustrated implementation includes two of the slots 150. A distal end 152 of the legs 146 are configured to be removably positioned in abutment with an engagement surface 154 of the hub 42 of the access cannula 34. With the access cannula 34 generally extending upwardly from the back of the patient positioned prone on the operative table, the spacer lock 40 is configured to rest upon the engagement surface 154 under the influence of gravity without any additional coupling mechanism. Further, the slots 150 are sized and shaped to slidably receive the wings 76 of the hub 72 of the sheath device 36. A distance between the legs 146 may be larger than a distance between the flats 74 of the hub 72 of the access cannula 34 such that, with the wings 76 of the hub 72 slidably received within the slots 150, each of the legs 146 is disposed adjacent a respective one of the flats 74.

Figure 14:
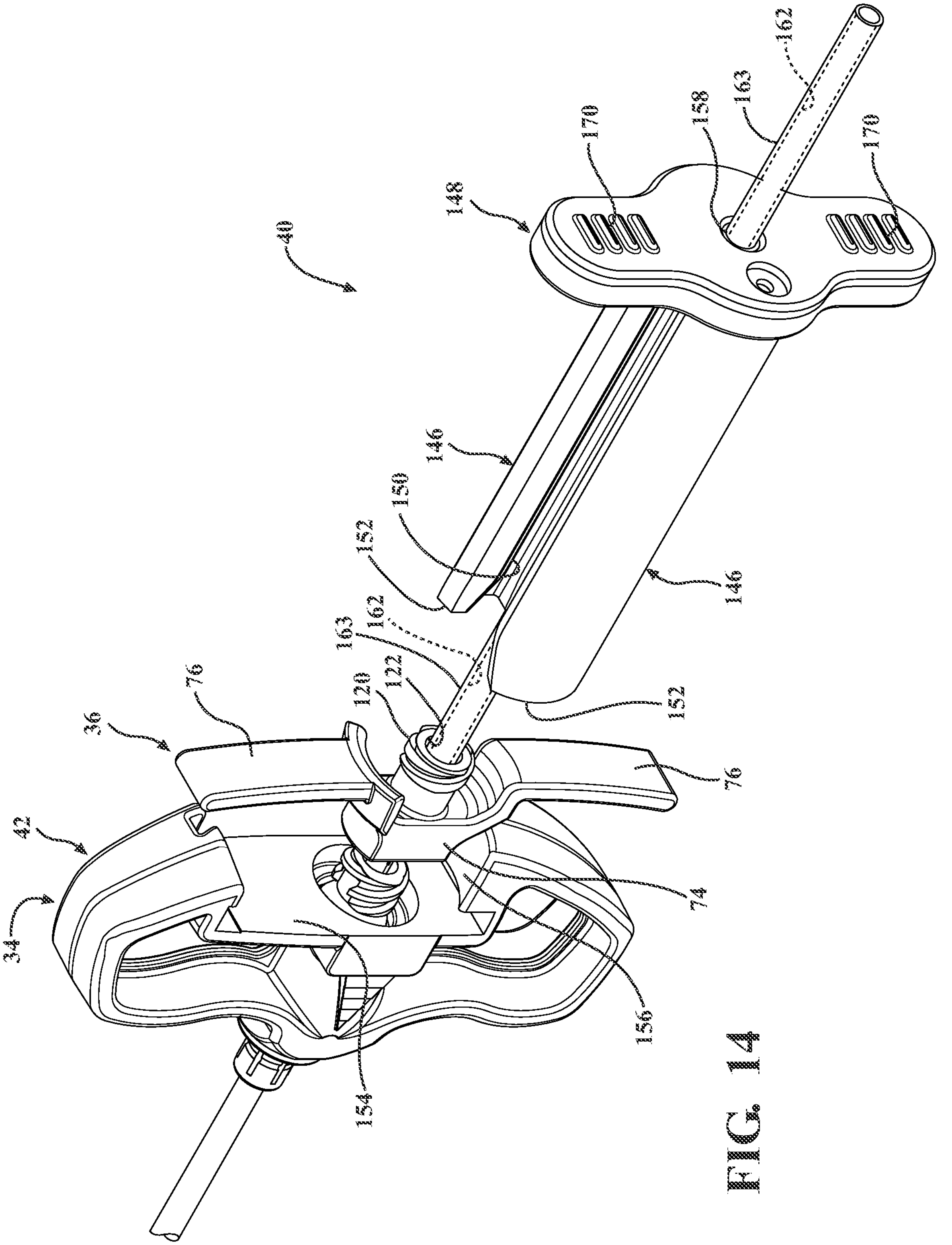
FIG. 14 is a rear perspective view of a portion of the access cannula and the sheath device, wherein a spacer lock is shown to be positionable in engagement with a hub of the access cannula and defining at least one slot sized to receive a hub of the sheath device.
Figure 15:
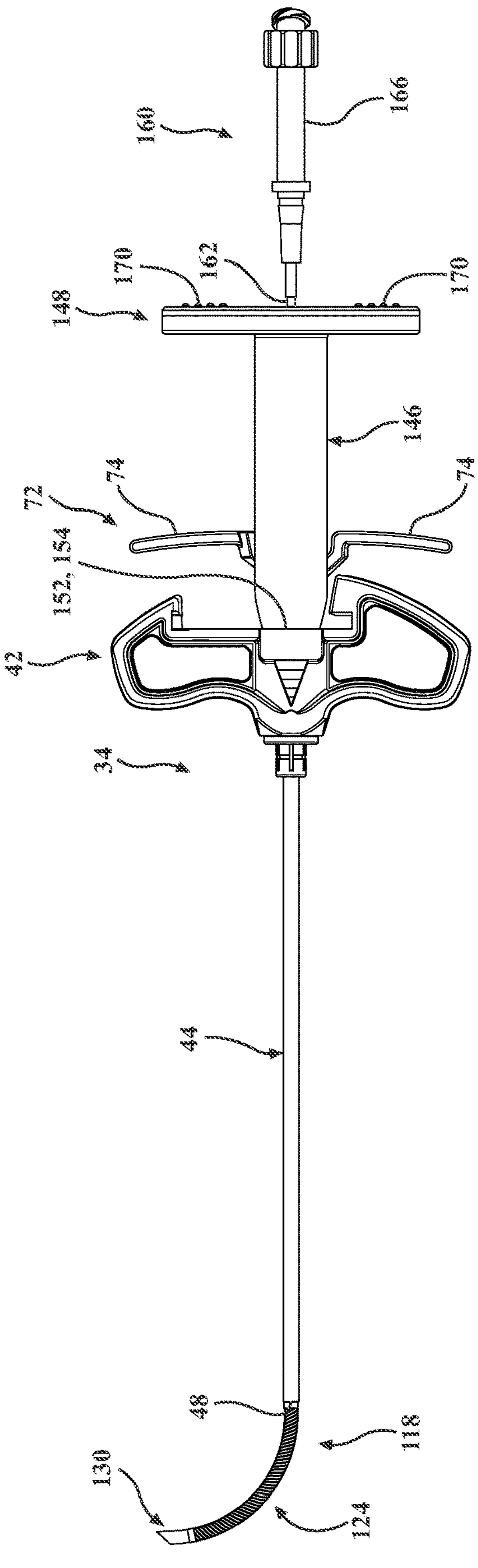
FIG. 15 is an elevation view of the system with the spacer lock in the first position, and a cavity-forming device operably coupled so as to position an expandable member within the flexible region of the sheath.

The hub 42 of the access cannula 34 may include at least one handle 156 extending from and positioned proximal to the engagement surface 154. The handle 156 extends between opposing sides of the hub 72, as best shown in FIG. 14. The distal end 152 of the legs 146 are configured to be removably positioned in abutment with the engagement surface 154 of the hub 42 adjacent the handle 156. Further, the hub 72 of the sheath device 36 is configured to be disposed within the slots 150 of the spacer lock 40, the spacer lock 40 is prevented from "tipping," laterally or otherwise, relative to the access cannula 34. As a result, despite the spacer lock 40 not being fixedly or removably secured to the access cannula 34 (i.e., without any additional coupling mechanism), movement of the spacer lock 40 relative to the access cannula 34 is constrained in four degrees of freedom. The two degrees of freedom by which the spacer lock 40 may move relative to the access cannula 34 is proximal translation during removal of the spacer lock 40, and rotation about a longitudinal axis of the sheath device 36. The resulting arrangement is shown in FIG. 15. It is contemplated that each of the spacer lock 40 and the hub 42 of the access cannula 34 may include complementary coupling features (not shown), for example a releasable detent, configured to removably couple the spacer lock 40 to the access cannula 34.

The cavity-forming device 160 may be packaged as operably coupled to the spacer lock 40. The hub 148 of the spacer lock 40 defines an aperture 158 in communication with a void between the legs 146. The aperture 158 may be centered on the hub 148 and configured to be coaxially aligned with the fitting 120 of the hub 72 of the sheath device 36 and a fitting 43 of the hub 42 of the access cannula 34, as shown in FIG. 14. The aperture 158 is sized to receive the component of the system 30, in this case, a tube 162 of the cavity-forming device 160. Thus, the tube 162 extends through the aperture 158, and an expandable member 164 is directed through the fitting 120 of the hub 72 of the sheath device 36 and guided through the lumen 122 as the spacer lock 40 is moved into engagement with the access cannula 34. Alternatively, it is contemplated that the cavity-forming device 160 is not operably coupled to the spacer lock 40, and the spacer lock 40 may be positioned in engagement with the access cannula 34, after which the expandable member 164 is directed through the aperture 158, followed by the tube 162 and the fitting 120 of the hub 72. In either implementation of the workflow, the resulting arrangement is shown in FIG. 15.

The cavity-forming device 160 may include a support member 163 extending along at least a portion of the tube 162. As best shown in FIG. 14, the support member 163 is coaxially arranged on an outer diameter of the tube 162. In certain implementations, the support member 163 may extend from near the hub 166 to a location positioned distal the spacer lock 40 when the spacer lock 40 is positioned in engagement with the hub 42 of the access cannula 34. More particularly, the support member 163 may extend from a position proximal to the aperture 158 of the spacer lock 40 to a position distal to the fitting 120 of the sheath device 36 when the spacer lock 40 is positioned in engagement with the hub 42 of the access cannula 34. Whereas the tube 162 of the cavity-forming device 160 may be flexible, the support member 163 may be relatively rigid. In one example, the support member 163 is formed from a metal and/or hard polymer. As a result, the support member 163 effectively prevents the spacer lock 40 from "tipping," laterally or otherwise, relative to the access cannula 34, especially with the spacer lock 40 configured to rest upon the engagement surface 154 of the access cannula 34 generally extending upwardly from the back of the patient positioned prone on the operative table without any additional coupling mechanism.

Figure 16:
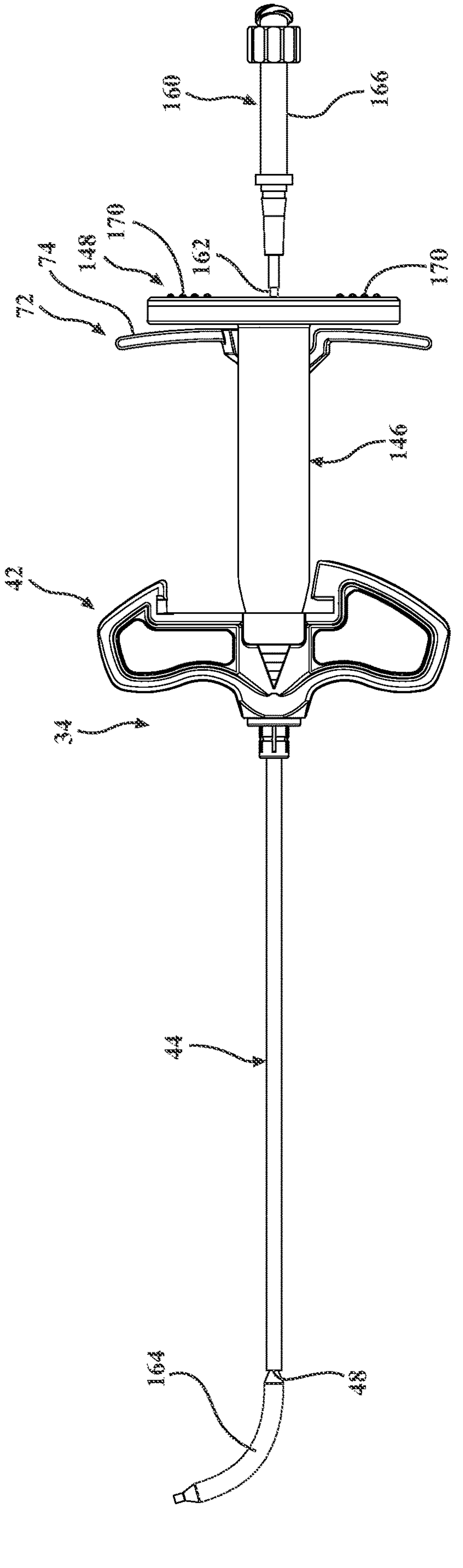
FIG. 16 is an elevation view of the system with the spacer lock in the second position so as to expose the expandable member within a curved path.

With further reference to FIG. 16, the tube 162 extends from a hub 166, and the expandable member 164 is disposed at a distal end of the tube 162. The hub 166 includes a fitting adapted to be coupled with a fluid line in communication with a source of incompressible fluid (not shown), for example, air. The expandable member 164 is configured to receive fluid from the source of fluid through the hub 166 and the tube 162 to be moved between a deflated state and an inflated state having a volume greater than the deflated state. In the deflated state, the expandable member 164 and the tube 162 are sized to be slidably inserted or directed through the lumen 122 of the sheath 118. A combined length of the tube 162 and the expandable member 164 may be approximately equal to the length of the sheath 118 such that, with the hub 166 positioned adjacent the hub 148 of the spacer lock 40, a distal end of the expandable member 164 is in registration with the distal end 130 of the sheath 118. Alternatively, the combined length may be such that the expandable member 164 is positioned beyond the distal end 130 of the sheath 118. The expandable member 164 is moved to the inflated state to compress or otherwise displace cancellous bone within the vertebral body at the target site. Returning the expandable member 164 to the deflated state may result in a cavity being formed within the cancellous bone for delivery of the curable material (see FIG. 21).

The tube 162 and/or the expandable member 164 are sufficiently flexible to follow the pathway defined by the lumen 122 of the sheath 118, including the flexible region 124 in the curved configuration. In other words, directing the expandable member 164 through the sheath 118 should not alter the curvature of the flexible region 124 of the sheath 118. Owing to the flexibility of the tube 162 and/or the expandable member 164, the cavity-forming device 160 may lack sufficient columnar strength to be advanced beyond the distal end 130 of the sheath 118 to penetrate the cancellous bone of the interior region. Additionally or alternatively, urging the cavity-forming device 160 to penetrate the cancellous bone may result in the trabeculae of the cancellous bone causing the expandable member 164 to deviate from the desired path previously created by the introducer device 32 and/or the target site previously accessed by the introducer device 32. The system 30 of the present disclosure advantageously provides for moving the sheath 118 relative to the cavity-forming device 160 in a manner to unsheathe and sheathe the expandable member 164. The spacer lock 40 provides for the unsheathing and sheathing the expandable member 164 with a syringe-style input that is both ergonomic and intuitive to the practitioner. The presence of the support member 163 facilitates the syringe-style input by supporting the tube 162 of the cavity-forming device 160 above a proximal side of the spacer lock 40.

The spacer lock 40, in cooperation with the hub 72 of the sheath device 36, facilitates the syringe-style input. With continued reference to FIGS. 16 and 17, the spacer lock 40 is configured to facilitate proximal and distal movement of the sheath 118 relative to the access cannula 34 while maintaining a position of the cavity-forming device 160 relative to the access cannula 34. The result includes proximal and distal movement of the sheath 118 including the sheath 118 relative to the cavity-forming device 160 including the expandable member 164, hence unsheathing and sheathing the expandable member 164, respectively. It is to be understood that the spacer lock 40 is an optional feature of the system 30, and more conventional methods may also be utilized.

FIG. 15 shows the sheath device 36 in a first position in which the hub 72 of the sheath device 36 is near the hub 42 of the access cannula 34, and the flexible region 124 is exposed beyond the distal end 48 of the access cannula 34. The distal end of the expandable member 164 is in registration with the distal end 130 of the sheath 118 such that the expandable member 164 is at least partially disposed within the flexible region 124 of the sheath 118. The hub 148 of the spacer lock 40 includes at least one grip surface 170. The hub 148 may include two grip surfaces 170 positioned opposite the aperture 158. The grip surfaces 170 are sized to be engaged by a thumb of the practitioner, and the grip surfaces 170 may include raised features configured to facilitate the same. The wings 76 of the hub 72 are oriented parallel to the grip surfaces 170, and the wings 76 are configured to be engaged by finger(s) of the practitioner. In one example, one of the wings 76 is configured to be engaged by the index finger of the practitioner, the other one of the wings 76 is configured to be engaged by the middle finger of the practitioner. With the thumb concurrently engaging one of the grip surfaces 170, the result is the aforementioned syringe-style input. The syringe-style input is economic and well-known to practitioners. As a result, the practitioner may intuitively squeeze the fingers towards the thumb to move the hub 72 and the sheath 118 from the first position to a second position in which the hub 72 is positioned relative to the first position. As shown in FIG. 16, the hub 72 of the sheath device 36 is positioned nearer or adjacent to the hub 148 of the spacer lock 40 in the second position. The hub 72 may be moved a desired distance, and/or a set distance until contacting the hub 148 of the spacer lock 40. The set distance may correspond to at least the distance required to unsheathe the expandable member 164 based on its length. The movement of the sheath 118 relative to the access cannula 34 and the cavity-forming device 160 exposes the expandable member 164 at the target site. The expandable member 164, as shown, occupies the curve previously assumed by the flexible region 124 of the sheath 118. The expandable member 164 remains on the curve owing to the curved path created during deployment of the introducer device 32 as well as the cancellous bone defining the curved path. The expandable member 164 is unsheathed and exposed within the interior region of the vertebral body in the deflated state, after which the expandable member 164 may be moved to the inflated state to displace the cancellous bone.

Figure 19:
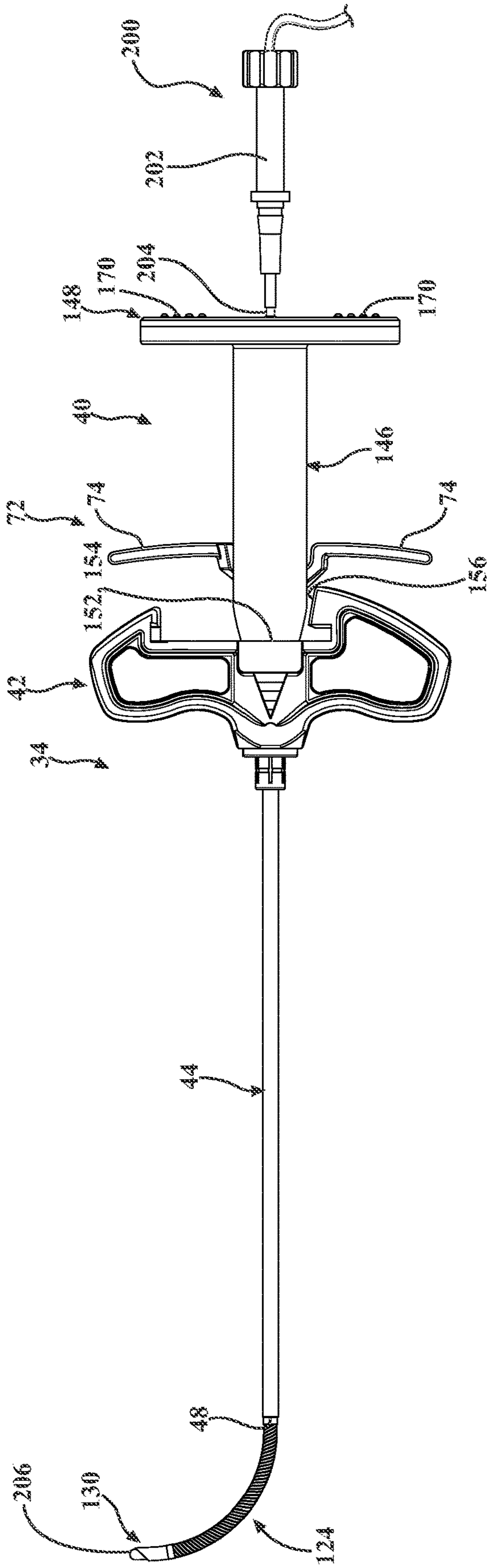
FIG. 19 is an elevation view of the system with the spacer lock in the first position, and an electrode probe operably coupled so as to position emitter(s) within the flexible region of the sheath.

The expandable member 164 is returned to the deflated state to form the cavity within the cancellous bone for delivery of the curable material (see FIG. 19). The expandable member 164 is sheathed. In one example, with the expandable member 164 deflated, the hub 72 is moved from the second position to the first position in which the flexible region 124 again is exposed beyond the distal end 48 of the access cannula 34 and the expandable member 164 is again at least partially disposed within the flexible region 124 of the sheath 118. In another example, a proximal input may be provided to the expandable member hub 166 to move moving the expandable member 164 into and through the sheath 118, after which the hub 72 is moved from the second position to the first position to reassume the curve with the distal end 130 of the sheath 118 is at the target site. With the expandable member 164 sheathed, it may be removed from the access cannula 34.

A vertebral augmentation kit including the introducer device 32, the access cannula 34, the sheath device 36, the spacer lock 40, and the cavity-forming device 160. In certain implementations, the kit may include more than one cavity-forming device 160. In particular, each of the cavity-forming devices 160 may include an expandable member 164 of a different dimension, which may be selectively deployed based on a desired cavity size and/or anatomical dimensions of the vertebral body of the patient. For example, the kit may include three cavity-forming devices 160 having expandable members 164 with axial length of 15 millimeters (mm), 20 millimeters, and 30 millimeters. Given that the sheath 118 of the sheath device 36 has a fixed length, the differing lengths of the expandable members 164 may necessitate selective adjustment of the cavity-forming device 160 relative to the sheath device 36 in order to properly unsheathe the expandable member 164. Additionally or alternatively, the spacer lock 40 of the present system 30 advantageously provides for maintaining a selective position of the cavity-forming device 160 during unsheathing of the expandable member 164. As such, the practitioner may selectively position the expandable member 164 (and/or treatment device) contralaterally, midline, or ipsilaterally, and the spacer lock 40 maintains the position as the practitioner performs other steps of the vertebral augmentation procedure.

Figure 17:
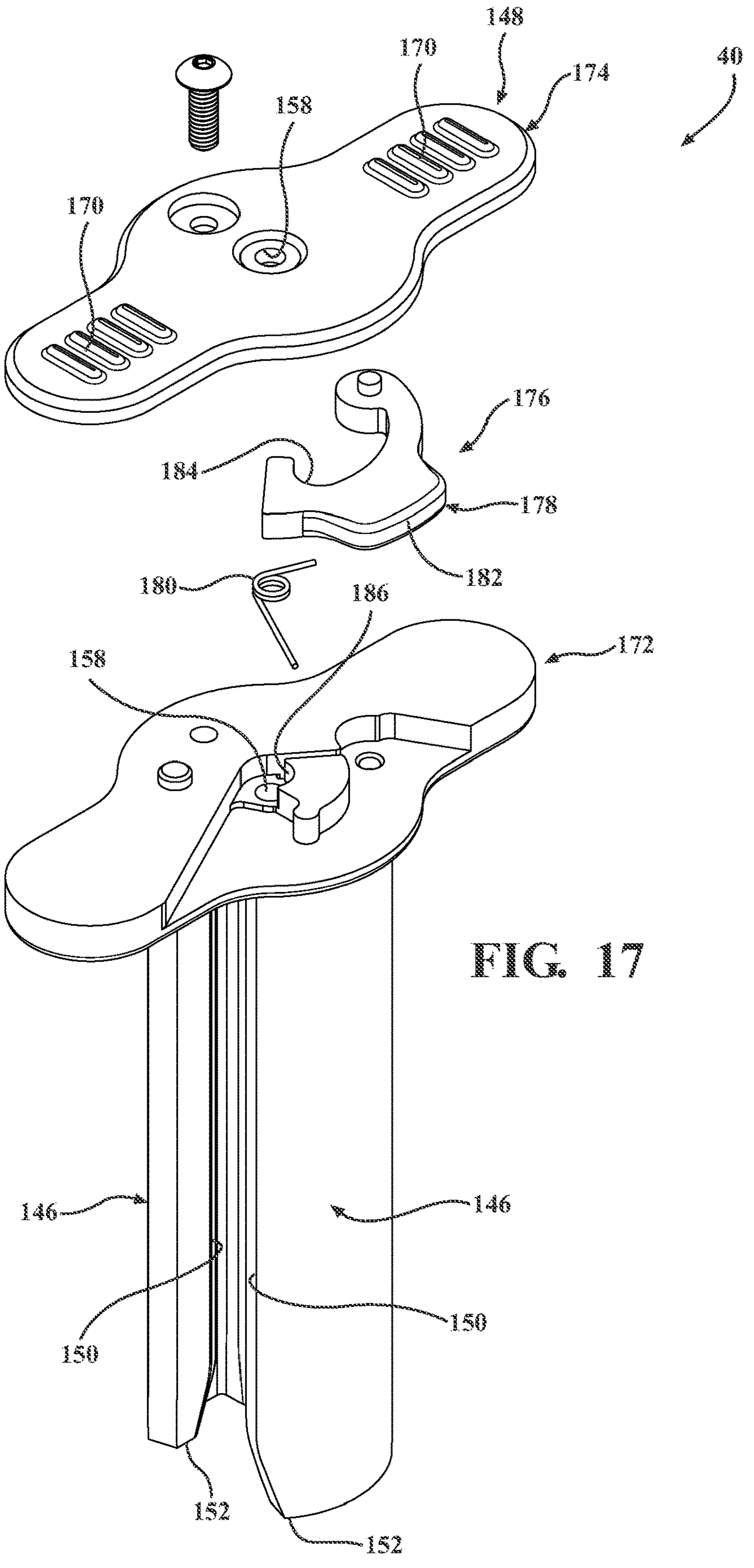
FIG. 17 is an exploded view of an implementation of the spacer lock.

Referring now to FIG. 17, the spacer lock 40 includes the hub 148, and the legs 146 extending from the hub 148. The hub 148 defines the aperture 158, and the legs 146 define the void space in communication with the aperture 158. The hub 148 includes a lower housing 172 from which the legs 146 extend, and an upper housing 174 secured to the lower housing 172. A lock mechanism 176 is operably coupled to the lower and upper housings 172, 174, and includes a lock actuator 178. The lock mechanism 176 includes a biasing element 180, for example, a torsion spring shown in FIG. 17. The lock actuator 178 may be a U-shaped component including an input surface 182 and a first lock surface 184. The lock actuator 178 is pivotally coupled to the hub 148, in particular the lower and upper housings 172, 174. The lower housing 172 includes a second lock surface 186. The first and second lock surfaces 184, 186 at least partially surround the aperture 158 of the lower housing 172. The biasing element 180 is operably coupled to the lower housing 172 and the lock actuator 178, and the biasing element 180 is configured to bias the lock actuator 178 to a closed state in which a shaft of the treatment device is effectively squeezed between the first and second lock surfaces 184, 186. The torsion spring biases the first lock surface 184 towards the second lock surface 186 to engage the shaft of the treatment device.

The lock actuator 178, in particular the input surface 182, is configured to receive an input from a user to selectively permit movement of the treatment device relative to the access cannula 34 or the sheath device 36. With continued reference to FIG. 17, the input to the input surface 182 pivots the lock actuator 178 against the bias of the biasing element 180 to move the lock mechanism from the closed state to an open state in which the distance between the first and second lock surfaces 184, 186 is increased. The increase in distance lessens or eliminates the squeezing on the treatment device, after which the treatment device may be selectively moved relative to the spacer lock 40. For example, the input surface 182 may be actuated with one hand of the practitioner, and with the other hand the practitioner proximally retracts the treatment device. Once positioned as desired, the practitioner merely removed the input to the input surface 182, after which the biasing element 180 returns the lock mechanism 176 from the open state to the closed state in which movement of the treatment device is again prevented.

Figure 18:
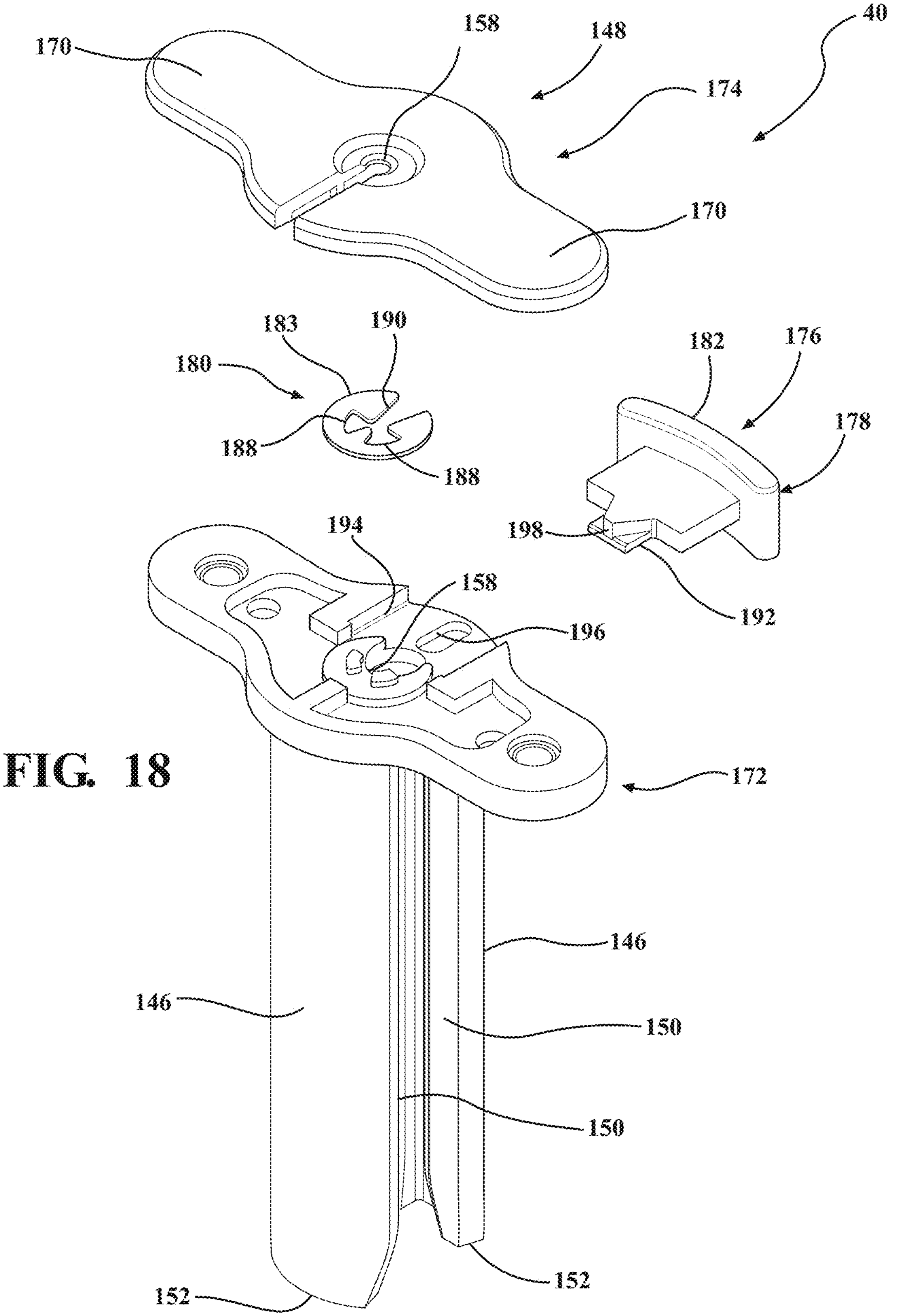
FIG. 18 is an exploded view of another implementation of the spacer lock.

FIG. 18 shows another implementation of the spacer lock 40. The lock mechanism 176 includes the lock actuator 178 having the input surface 182, and the biasing element 180 operably coupled to the lock actuator 178 and the hub 148. The biasing element 180 may be a disc 183 having an opening and slots 188, 190 extending radially from the opening. The disc 183 may be coupled to the lower housing 172 such that the opening is coaxially aligned with the aperture 158. One of the slots 190 extends to the outer edge of the disc 183, and the other slots 188 result in thinned regions of the disc 183 that are configured to resiliently deflect when engaged by the lock actuator 178. In a natural or closed state, a size of the opening is slightly smaller than a shaft of the treatment device such that the treatment device is prevented from moving relative to the spacer lock 40. The shaft of the treatment device is effectively "pinched" between tips of flanges defined by the slots 188, 190. For example, the tips of flanges defined by the slots 188, 190 pinches the support member 163 of the cavity-forming device 160.

The lock actuator 178 is slidably coupled to the hub 148. The lock actuator 178 may include rails 192 configured to engage slots 194 of the lower housing 172. A pin (not shown) slidably disposed with a cavity 196 permits the slidable movement of the lock actuator 178 relative to the lower housing 172, but prevents the lock actuator 178 from decoupling from the same. The lock actuator 178 may include a protrusion 198 shaped complementary to the slot 190. In the illustrated implementation, the slot 190 and the protrusion 198 are complementarily triangular when viewed in plan. In the natural or closed state, the protrusion 198 is positioned within the slot 190, and the position of the shaft of the treatment device is maintained by engagement of the tips of flanges defined by the slots 188, 190. For example, the tips of flanges defined by the slots 188, 190 pinches the support member 163 of the cavity-forming device 160. An input may be provided to the input surface 182 to move the lock mechanism 176 from the natural or closed state to the open state in which movement of the treatment device is permitted relative to the spacer lock 40. The lock actuator 178 is slidably moved relative to the hub 148, and the protrusion 198 forces the thinned regions of the disc 183 to resiliently deflect, for example, radially outward relative to the aperture 158. The resilient deflection of the thinned regions results in a diameter of the opening to increase in the open state by an extent sufficient to permit movement of the shaft of the treatment device relative to the spacer lock 40. Once the treatment device has been moved to the desired position, the input to the input surface 182 is removed. The potential energy stored in the resiliently deflected thinned regions of the disc 183 is released, and the lock actuator 178 is slidably moved relative to the hub 148 to an initial position. The lock mechanism 176 is returned to the natural or closed state, after which further movement of the treatment device relative to the spacer lock 40 is prevented. The above steps may be repeated as many times as desired.

An exemplary workflow of the spacer lock 40 will now be described in the context of the cavity-forming device 160 during a kyphoplasty procedure. The introducer device 32 and the sheath device 36 are deployed, and the introducer device 32 is removed from the sheath device 36. The cavity-forming device 160 is directed through the aperture 158 of the spacer lock 40 either before or after operably positioning the spacer lock 40 in engagement with the hub 42 of the access cannula 34. With the hub 166 engaging the hub 148 of the spacer lock 40, the distal end of the expandable member 164 may be in registration with the distal end 130 of the sheath 118. The lock mechanism 176 is in the closed state such that engagement of the tube 162 by the lock actuator 178 prevents movement of the cavity-forming device 160 relative to the spacer lock 40 (and thus also relative to the access cannula 34 and the sheath device 36). Using the syringe-style input, the expandable member 164 is unsheathed in a contralateral position within the vertebral body. In particular, because the spacer lock 40 engages the support member 163 and/or the tube 162, moving the hub 72 of the sheath device 36 within the slots 150 of the spacer lock 40 results in corresponding movement of the distal end 130 of the sheath 118 to expose the expandable member 164 at the target site. The expandable member 164 is inflated to create a cavity within the vertebral body. In one example, the practitioner may wish to create a second cavity that is positioned ipsilaterally to the midline. After resheathing the expandable member 164, the input is provided to the input surface 182 of the spacer lock 40 to move the lock mechanism 176 from the closed state to the open state. With the lock mechanism 176 in the open state, another input provided to the hub 166 proximally retracts the cavity-forming device 160 to the desired position. The input is released, and the lock mechanism 176 returns to the closed state. Again, using the syringe-style input, the expandable member 164 is unsheathed in the ipsilateral position within the vertebral body. During both instances where the expandable member 164 is unsheathed, the practitioner need not separately maintain the position of the cavity-forming device 160, thereby freeing him or her to focus on other aspects of the procedure.

In another example with the cavity-forming device 160, the practitioner may decide that the 30-millimeter expandable member is indicated. Given the relative size of the expandable member 164 relative to the vertebral body, it may be necessary to position the expandable member 164 on the midline of the vertebral body. As mentioned, however, the distal end 130 of the sheath 118 may be positioned contralaterally when deployed, and the distal end of the expandable member 164 may be in registration with the distal end 130 of the sheath 118. In order to position the expandable member 164 on the midline of the vertebral body, a slight proximal retraction of the cavity-forming device 160 may be indicated. The spacer lock 40 facilitates the proximal retraction of the cavity-forming device 160 without the practitioner needing to manually maintain its position, which is particularly beneficial during the subsequent unsheathing the expandable member 164 on the midline.

Another exemplary workflow of the spacer lock 40 will now be described in the context of an electrode probe 200 during a tissue ablation procedure. Referring to FIG. 19, the electrode probe 200 may include a hub 202, a shaft 204, and at least one emitter 206 at the end of the shaft 204. The electrode probe 200 is configured to be coupled to a source of electrical energy, and to provide the energy at the target site to ablate tissue. The tissue to be ablated may be a tumor, a nerve, or the like. In one example, the tissue may be the basivertebral nerve having a main branch that extends anteriorly to within the vertebral body generally along the midline of the same. As such, with the introducer device 32 configured to access contralateral positions within the vertebral body, the system 30 is well suited to ablate the basivertebral nerve. The introducer device 32 and the sheath device 36 are deployed, and the introducer device 32 is removed from the sheath device 36. The electrode probe 200 is directed through the aperture 158 of the spacer lock 40 either before or after operably positioning the spacer lock 40 in engagement with the hub 42 of the access cannula 34. With the electrode hub 202 engaging the hub 148 of the spacer lock 40, the distal end of the emitter(s) 206 may be in registration with the distal end 130 of the sheath 118. This contralateral positioning of the emitter(s) 206 may be sub-optimal for ablation of the basivertebral nerve. As a result, the input is provided to the input surface 182 of the spacer lock 40 to move the lock mechanism 176 from the closed state to the open state. With the lock mechanism 176 in the open state, another input provided to the electrode hub 202 to adjust the emitter(s) 206 to the desired position. The input is released, and the lock mechanism 176 returns to the closed state. Using the syringe-style input, the emitter(s) 206 is unsheathed in the desired position within the vertebral body. The emitter(s) 206 is powered to supply electrical energy to ablate the basivertebral nerve.

Figure 20:
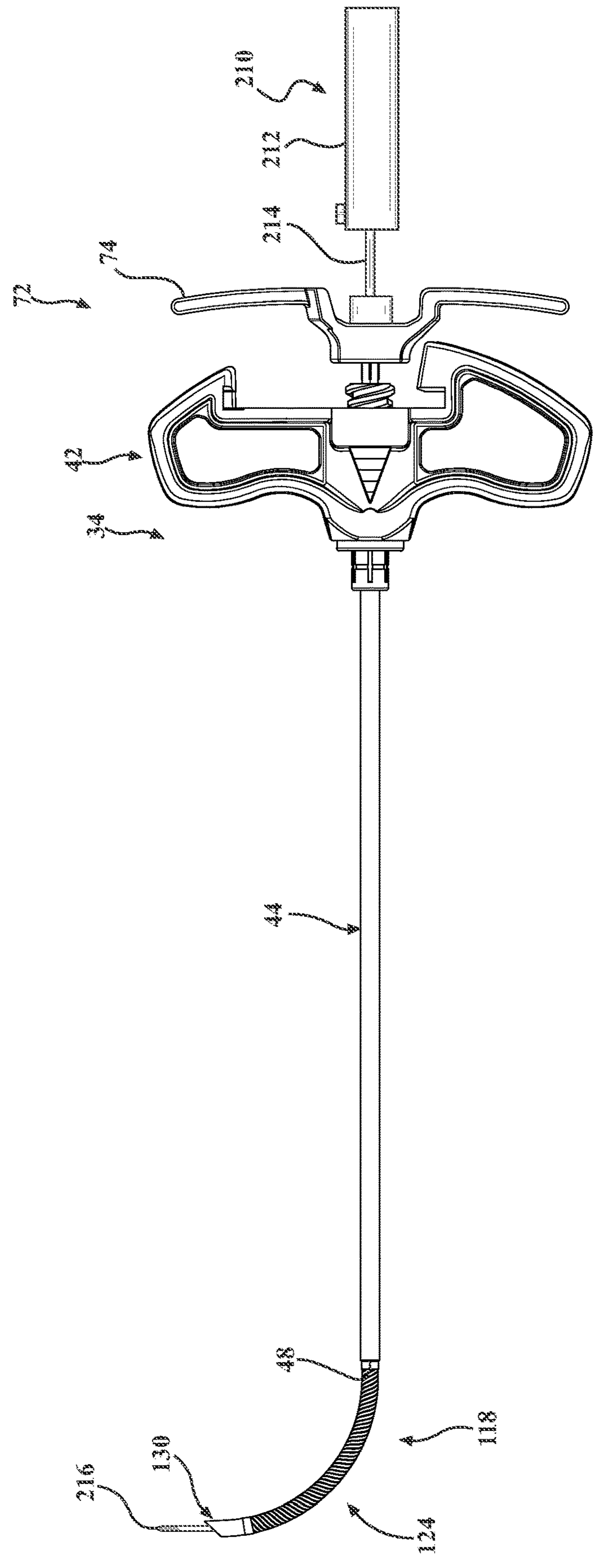
FIG. 20 is an elevation view of the system with the spacer lock removed, and a drill device operably coupled to the sheath device so as to direct a drill tip through the sheath.

It is understood that the ablation of tissue is an optional step, and it may occur before or after creation of the cavity with the cavity-forming device 160. Further, it may be desirable to drill a bore within the vertebral body prior to or after positioning of the emitter(s) 206 and/or the expandable member 164 of the cavity-forming device 160. For example, the introducer device 32, the sheath device 36, the cavity-forming device 160, and/or any other component of the system 30 may encounter a bone tumor. In order to access within the tumor for optimal placement of the emitter(s) 206, a drill device 210 may be directed through the sheath 118. FIG. 20 shows the drill device 210 including a handpiece 212, a shaft 214 extending from the handpiece 212, and a drill tip 216 coupled to the shaft 214. The shaft 214 includes a flexible region configured to navigate the curve assumed by the flexible region 124 of the sheath 118. The drill device 210 may be deployed beyond the distal end 130 of the sheath 118, and operated to resect the tumor. The drill device may be powered or manual. One exemplary drill device is the MicroFX Osteochondral Drilling (OCD) system manufactured by Stryker Corporation (Kalamazoo, Mich.). A manual drill device may include a knurled handle. The introducer device 32, the sheath device 36, the cavity-forming device 160, and/or any other component of the system 30 may encounter necrotic tissue. In order to access within the vertebral body for optimal placement of the emitter(s) 206 for ablation of the basivertebral nerve, the drill device 210 may be used in the aforementioned manner. It is understood that the drill device 210 and corresponding workflow steps are optional. It is further contemplated that a biopsy needle may be used in the aforementioned manner to obtain a tissue sample for biopsy. The biopsy needle may include a flexible region configured to navigate the curve assumed by the flexible region 124 of the sheath 118. The biopsy needle may be deployed beyond the distal end 130 of the sheath 118, and operated to, for example, obtain a core sample of the tumor.

The workflow may include delivering curable material (also known as bone cement) to within the vertebral body. This may be done with or without creating a cavity to receive the curable material. A curable material delivery system suitable for use with the system 30 of the present disclosure is described in commonly-owned International Patent Publication No. WO2019/200091, published Oct. 17, 2019, and U.S. Pat. No. 6,547,432, issued Apr. 15, 2003, the entire contents of which are hereby incorporated by reference, and sold under the tradename PCD System by Stryker Corporation (Kalamazoo, Mich.). Still another suitable cement delivery system is disclosed in commonly owned U.S. Pat. No. 7,658,537, issued Feb. 9, 2010, the entire contents of which are hereby incorporated by reference.

Figure 21:
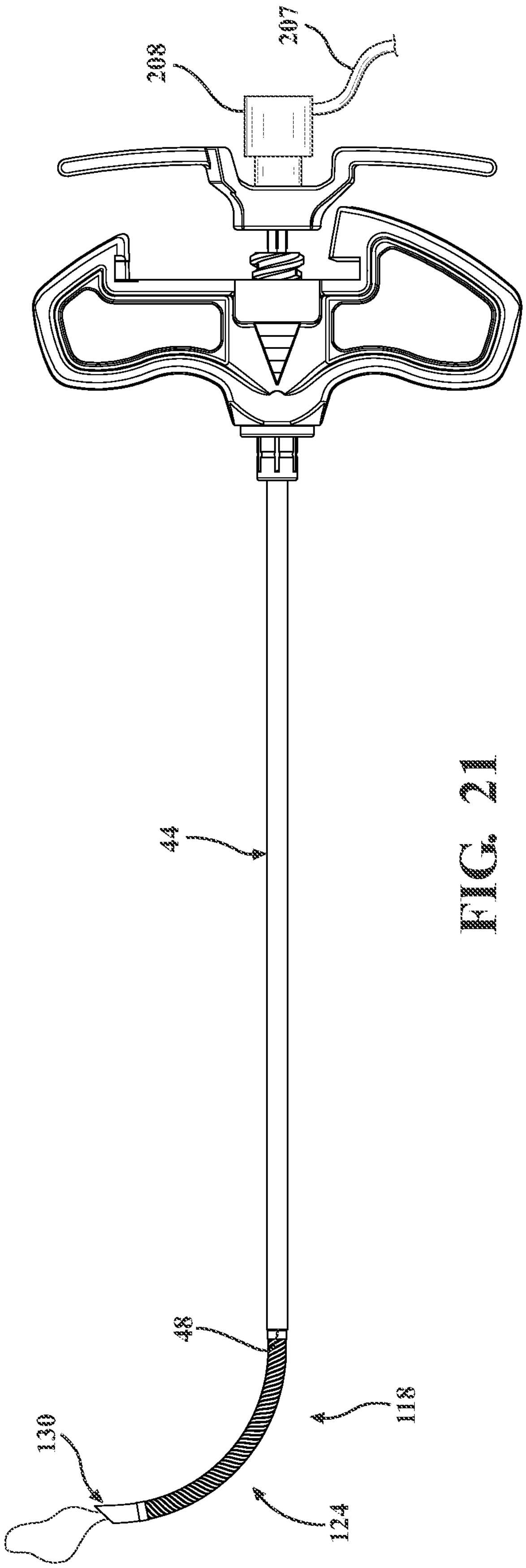
FIG. 21 is an elevation view of the system with the spacer lock removed, and a curable material delivery device operably coupled to the sheath device so as to direct curable material through the sheath.

Referring to FIG. 21, the cement delivery system may include a tube 207 and a coupler 208 is adapted to be coupled to the fitting 120 of the sheath hub 72, as shown in FIG. 20. Curable material is delivered through the sheath 118 to the target site. During the delivery the curable material, the hub 72 of the sheath device 36 may be moved from the first position to the second position such that the sheath 118 may be proximally retracting while the curable material is being delivered in a retrograde manner. The sheath 118 is removed from the access cannula 34. The trocar may be reintroduced through the access cannula 34, and the access cannula 34 and trocar removed from the vertebral body. The overlying tissue may be sutured.

Referring now to FIGS. 22A-25C, various configurations for deploying the treatment device within the vertebral body with a bipedicular approach are illustrated. As previously discussed, certain aspects of the disclosure are directed to accessing the contralateral side of the vertebral body through a unipedicular approach. For another example, certain aspects of the present disclosure are directed to accessing the midline through a unipedicular approach for ablation of the basivertebral nerve. Utilizing the bipedicular approach in which there are two of the systems 30 of the present disclosure advantageously provides access to nearly all regions of the interior of the vertebral body. The illustrated figures show a schematic representation of the treatment device within the vertebral body, for example, after being deployed through the sheath 118 as previously explained. In a preferred implementation, the treatment device is representative of the electrode probe 200 previously described, in which the emitters 206 of each of the electrode probes 200 are configured to be deployed in complementary configurations within the vertebral body to effectuate desired heating patterns once operated. One exemplary electrode probe that is sufficiently flexible for navigating the curved distal portion is described in United States Patent Publication No. 2013/0006232, published Jan. 3, 2013, the entire contents of which are hereby incorporated by reference. The electrode probe 200 may be bipolar or monopolar. It is contemplated that the electrode probe 200 may be irrigated such that a fluid is infused into the adjacent tissue prior to and/or during ablation. It is further contemplated that the electrode probe 200 may be cooled, for example, by circulating a fluid within pathways internal to the electrode probe 200.

Figure 22A:
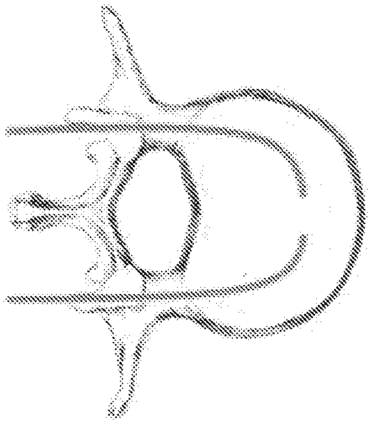
FIG. 22A-22C are views of vertebra with a schematic representation of treatment devices being deployed off-axis and ipsilaterally.
Figure 22B:
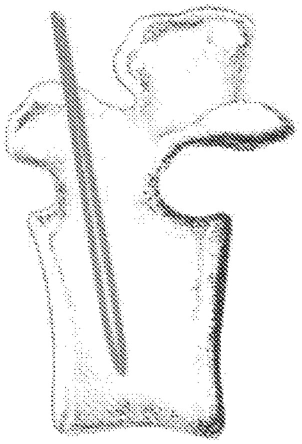
Figure 22C:
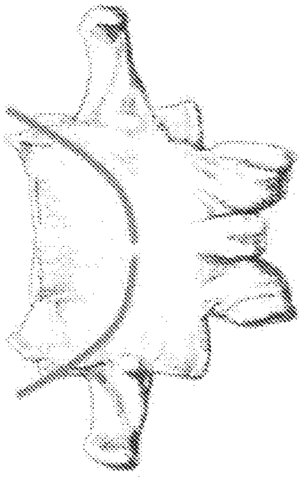

FIGS. 22A-22C illustrates a bipedicular approach in which each of the systems 30 are used to deploy the treatment devices ipsilaterally. Should this be known preoperatively, the angle of approach on the pedicles themselves may be adjusted owing to the curve anticipated to be assumed by the system 30 and ultimately the treatment device. Should this be desired after the access cannula 34 (and trocar) are deployed within the pedicle of the vertebral body, then adjustments may be made to the position the distal end 48 of the access cannula 34 at a specific point within the (bony) pedicle in anticipation of the curve of the introducer device 32, which, in certain implementations, is known and reproducible. FIG. 22A shows each of the treatment devices positioned ipsilaterally and symmetrical about the midline of the vertebral body. Further, ends of the treatment devices are substantially in the same position in the anterior-posterior direction. FIGS. 22B and 22C show each of the treatment devices positioned substantially in the same position in the caudio-cranial direction.

Figure 23A:
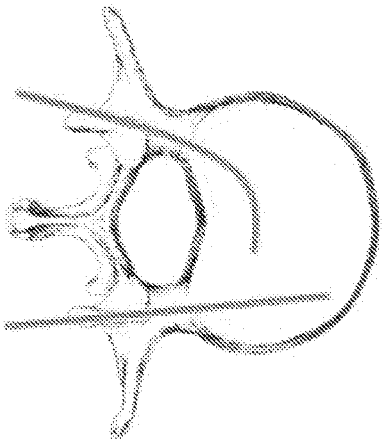
FIG. 23A-23C are views of vertebra with a schematic representation of treatment devices with one of the treatment devices being deployed on-axis and ipsilaterally and another one of the treatment devices being deployed off-axis and contralaterally.
Figure 23B:
Figure 23C:
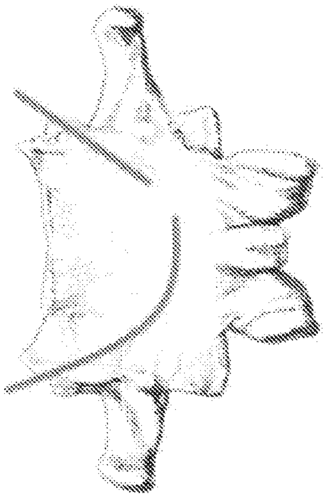

FIGS. 23A-23C illustrate a bipedicular approach in which the systems 30 are used to deploy one of the treatment devices ipsilaterally and the other one of the treatment devices contralaterally. The treatment device deployed ipsilaterally is on-axis, whereas the treatment device deployed contralaterally is curved in manners previously described. FIG. 23A shows the end of the on-axis treatment device positioned anteriorly relative to the end of the off-axis treatment device. The reverse configuration is contemplated. FIG. 23C shows the end of the on-axis treatment device positioned cranially relative to the end of the off-axis treatment device. The reverse configuration is contemplated.

Figure 24A:
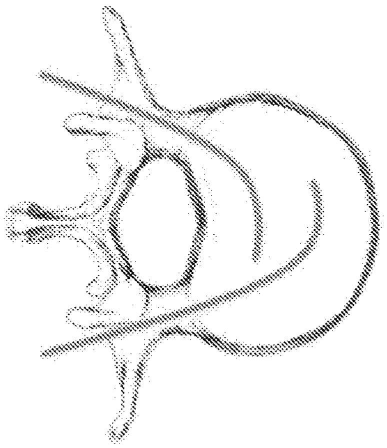
FIG. 24A-24C are views of vertebra with a schematic representation of treatment devices being deployed off-axis and contralaterally.
Figure 24B:
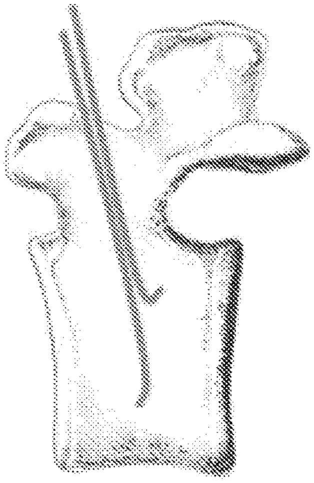
Figure 24C:
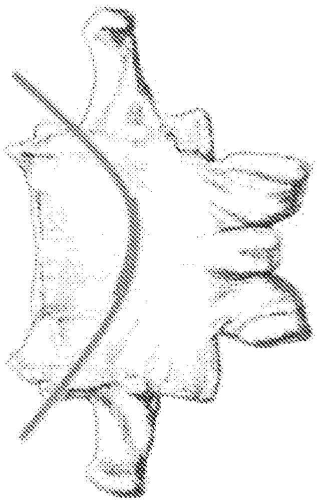

FIGS. 24A-24C illustrate a bipedicular approach in which each of the systems 30 are used to deploy the treatment devices contralaterally. The treatment devices are deployed off-axis and may be considered to overlap in the medio-lateral direction. FIG. 24A shows the end of one the treatment devices positioned anteriorly relative to the end of the other treatment device. The reverse configuration is contemplated. FIGS. 24B and 24C show each of the treatment devices positioned substantially in the same position in the caudio-cranial direction.

Figure 25A:
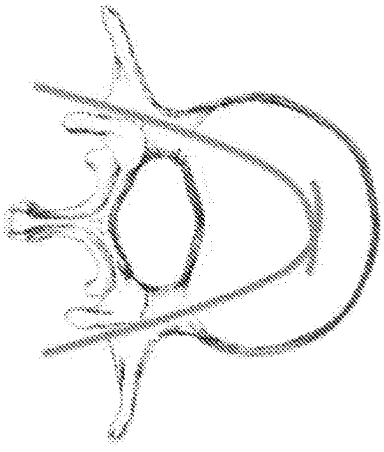
FIG. 25A-25C are views of vertebra with a schematic representation of treatment devices being deployed off-axis and contralaterally.
Figure 25B:
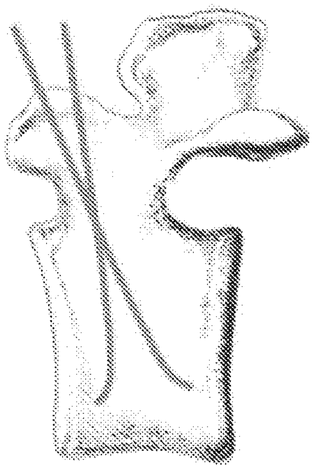
Figure 25C:

FIGS. 25A-25C illustrate a bipedicular approach in which each of the systems 30 are used to deploy the treatment devices contralaterally. The treatment devices are deployed off-axis and may be considered to overlap in the medio-lateral direction. FIG. 25A shows the ends of the treatment devices being substantially in the same position in the anterior-posterior direction. FIGS. 25B and 25C show an end of one of the treatment devices positioned cranially relative to the end of the other treatment device. The reverse configuration is contemplated.

Exemplary Clauses

Clause 1—A method of augmenting a vertebral body with a system including (i) an access cannula, (ii) an introducer device including an actuator, a shaft including a proximal portion that is rigid and a distal portion that is articulable, and a pulling element coupled to the actuator, and (iii) a sheath including a flexible region, the method including: positioning a distal end of the access cannula within the vertebral body such that a lumen of the access cannula provides access to an interior region of the vertebral body along a longitudinal axis; directing the shaft of the introducer device and the sheath to within the access cannula such that the distal portion of the introducer device and the flexible region of the sheath remains within the access cannula, wherein the introducer device is in an unconstrained state in which the pulling element is at a first tension; thereafter, providing an input to the actuator to move the introducer device from the unconstrained state to a constrained state in which the pulling element is at a second tension greater than the first tension, wherein the access cannula prevents the distal portion of the shaft and the distal portion of the sheath from assuming a curve from the longitudinal axis; and thereafter, advancing the introducer device and the sheath device relative to the access cannula with the introducer device in the constrained state such that the distal portion of the introducer device and the distal portion of the sheath assume the curve within the vertebral body with advancement beyond the distal end of the access cannula.

Clause 2—The method of clause 1, wherein the distal portion of the introducer device and the flexible region of the sheath and configured to plunge through cancellous bone within the vertebral body while assuming the curve.

Clause 3—The method of clauses 1 or 2, wherein the step of directing the shaft and the sheath further includes positioning a distal end of the sheath in registration with the distal end of the access cannula.

Clause 4—The method of clause 3, further including aligning indicia disposed on the sheath with a hub of the access cannula so as to position the distal end of the distal portion in registration with the distal end of the access cannula.

Clause 5—The method of any one of clauses 1-4, further including: providing another input to the actuator to move the introducer device from the constrained state to the unconstrained state; and removing the introducer device from the sheath device, wherein the pulling element being at the first tension in the unconstrained state provides for removal of the introducer device from the sheath with the flexible region of the sheath remaining curved within the vertebral body.

Clause 6—The method of clause 5, wherein the system further includes a spacer lock defining an aperture and including legs defining slots, and a treatment device, the method further including: engaging the legs of the spacer lock with a cannula hub of the access cannula such that the aperture is aligned with the lumen, and a sheath hub of the sheath is disposed within the slots; and directing the treatment device through the aperture to within the sheath, wherein the treatment device is flexible to bend along the curve of the flexible region of the sheath disposed within the vertebral body.

Clause 7—The method of clause 6, further including: proximally moving the sheath hub within the slots of the spacer lock with corresponding movement of the sheath exposing the treatment device at a target location within the vertebral body; and performing augmentation of tissue of the vertebral body at the target location.

Clause 8—The method of clauses 6 or 7, wherein the treatment device is one of a cavity-forming device configured to displace tissue, an electrode probe configured to ablate tissue, a drill for cutting tissue, a tissue capturing device for tissue biopsy.

Clause 9—The method of any one of clauses 6-8, wherein the spacer lock includes a lock actuator and a lock mechanism operably coupled to the lock actuator, the method further including: providing an input to the lock actuator to disengage the lock actuator from a shaft of the treatment device; and moving the shaft of the treatment device within the aperture of the spacer lock to selectively adjust a position of the treatment device relative to the access cannula.

Clause 10—The method of clause 9, further including removing the input to the lock actuator to reengage the lock mechanism and the shaft of the treatment device, thereby preventing further movement of the treatment device relative to the access cannula.

Clause 11—The method of any one of clauses 7-10, wherein the sheath includes a metal tube, and a polymeric sleeve coupled to the metal tube and extending between opposing ends of the flexible region, the method further including: removing the treatment device from the sheath, wherein a curved path remains in the vertebral body that is along the curve previously assumed by the introducer device; and advancing the flexible region of the sheath relative to the distal end of the access cannula, wherein a preformed bend of the polymeric sleeve facilitates the flexible region following the curved path.

Clause 12—The method of clause 11, wherein the system includes a source of curable material, the method further including delivering the curable material through the sheath to within the vertebral body, wherein the polymeric sleeve prevents egress of the curable material through articulating features of the metal tube.

Clause 13—The method of clause 5, further including: after the step of removing the introducer device from the sheath, directing the shaft of the introducer device in the unconstrained state to within the sheath; and providing still another input to the actuator to move the introducer device from the unconstrained state to the constrained state so as to reestablish the curve of the flexible region; and removing the introducer device from the sheath with the introducer device in the unconstrained state.

Clause 14—A method of augmenting a vertebral body with a system including (i) an access cannula, (ii) an introducer device including a shaft including a proximal portion that is rigid and a distal portion that is articulable, (iii) a sheath device including a sheath hub and a sheath having a flexible region positioned along the distal portion of the shaft, and (iv) a spacer lock including legs defining slots, the method including: positioning a distal end of the access cannula within the vertebral body to provide access to an interior region of the vertebral body along a longitudinal axis; directing the shaft of the introducer device and the sheath to within the access cannula; operating the introducer device to cause the distal portion of the shaft and the flexible region of the sheath to assume a curve within the interior region of the vertebral body; removing the shaft from the sheath, wherein the flexible region of the sheath remains along the curve; thereafter, aligning the sheath hub with the slots of the spacer lock; positioning the legs of the spacer lock on an engagement surface of the access cannula such that the spacer lock is disposed within the slots, wherein rotation of the sheath relative to the spacer lock is prevented; and moving proximally the sheath hub within the slots to move the sheath relative to the access cannula.

Clause 15—The method of clause 14, wherein the system includes a cavity-forming device including a hub, a tube extending from the hub, and an expandable member disposed at the end of the tube, the method further including: directing the expandable member and the tube through an aperture in the spacer lock such that the expandable member is in registration with a distal end of the sheath and the hub contacts the spacer lock; and moving the sheath hub within the slots towards the hub so as to expose the expandable member beyond the distal end of the sheath.

Clause 16—The method of clauses 14 or 15, wherein the system includes an electrode probe including an electrode hub, an electrode shaft extending from the electrode hub, and a probe near an end of the electrode shaft, the method further including: directing the electrode shaft through an aperture in the spacer lock such that the probe is in registration with a distal end of the sheath and the electrode hub contacts the spacer lock; and moving the sheath hub within the slots towards the electrode hub so as to expose the probe beyond the distal end of the sheath.

Clause 17—The method of any one of clauses 14-16, further including: removing the cavity-forming device from the sheath; and decoupling the spacer lock and the cavity-forming device from the access cannula, thereby exposing a Luer fitting on the sheath hub.

Clause 18—The method of clause 15, wherein the spacer lock includes a lock actuator and a lock mechanism operably coupled to the lock actuator, the method further including: providing an input to the lock actuator to disengage the lock actuator from the tube of the cavity-forming device; and moving the tube within the aperture of the spacer lock to selectively adjust a position of the expandable member relative to the access cannula or the sheath.

Clause 19—A method of augmenting a vertebral body with a system including (i) an access cannula, (ii) an introducer device including a shaft including a distal portion that is articulable with a pulling element, a handle defining a proximal opening, a control member coupled to the pulling element and defining a control surface, a resilient arm extending from the control member, and a lock head at an end of the resilient arm and defining a release surface, and (iii) a sheath having a flexible region positioned over the distal portion of the shaft, the method including: positioning a distal end of the access cannula within the vertebral body to provide access to an interior region of the vertebral body along a longitudinal axis; grasping the handle of the introducer device; directing the shaft of the introducer device and the sheath within the access cannula such that the distal portion of the introducer device and the distal portion of the sheath are beyond the distal end of the access cannula; operating the introducer device by moving the control member relative to the handle to cause the pulling element to be tensioned to move the introducer device from an unconstrained state in which the distal portion of the shaft is oriented along the longitudinal axis, and a constrained state in which the distal portion assumes a curve away from the longitudinal axis, wherein a ramp of the handle is deflected as the resilient arm moves along the ramp and engages a retention feature of the handle; and depressing the release surface extending through the proximal opening to disengage the lock head from the retention feature to move the introducer device from the constrained state to the unconstrained state.

Clause 20—A method of augmenting a vertebral body with a system including (i) an access cannula, (ii) an introducer device including a shaft including a proximal portion that is rigid and a distal portion that is articulable, (iii) a sheath device including a sheath hub and a sheath having a flexible region positioned along the distal portion of the shaft, and (iv) a drill device including a flexible region, the method including: positioning a distal end of the access cannula within the vertebral body to provide access to an interior region of the vertebral body along a longitudinal axis; directing the shaft of the introducer device and the sheath beyond the access cannula; operating the introducer device to cause the distal portion of the shaft and the flexible region of the sheath to assume a curve within the interior region of the vertebral body; removing the introducer device from the sheath device with the flexible region of the sheath remaining in the curve; directing the drill device through the sheath device and resecting tissue within the vertebral body, thereby leaving a bore; and removing the drill device from the sheath device.

Clause 21—The method of clause 20, wherein the system includes an electrode probe including an electrode hub, an electrode shaft extending from the electrode hub, and a probe near the end of the electrode shaft, the method further including: directing the electrode shaft through the sheath; exposing the probe beyond the distal end of the sheath and within the bore; and operating the probe to ablate tissue within the vertebral body.

Clause 22—The method of clause 20, wherein the system includes a cavity-forming device including a hub, a tube extending from the hub, and an expandable member disposed at the end of the tube, the method further including: directing the expandable member through the sheath; exposing the probe beyond the distal end of the sheath and within the bore; inflating the expandable member to provide a cavity within the vertebral body; and deflating and then removing the expandable member from the sheath.

Clause 23—The method of clause 22, wherein the system includes a source of curable material, the method further including delivering the curable material through the sheath to within the cavity of the vertebral body.

Clause 24—A method of augmenting a vertebral body with a system including (i) an access cannula, (ii) an introducer device including a shaft including a proximal portion that is rigid and a distal portion that is articulable, (iii) a sheath device including a sheath hub and a sheath having a flexible region positioned along the distal portion of the shaft, and (iv) a biopsy device including a flexible region, the method including: positioning a distal end of the access cannula within the vertebral body to provide access to an interior region of the vertebral body along a longitudinal axis; directing the shaft of the introducer device and the sheath beyond the access cannula; operating the introducer device to cause the distal portion of the shaft and the flexible region of the sheath to assume a curve within the interior region of the vertebral body; removing the introducer device from the sheath device with the flexible region of the sheath remaining in the curve; directing the biopsy device through the sheath device and capture a tissue sample within the vertebral body; and removing the biopsy device from the sheath device.

Clause 25—A method of augmenting a bone with a system including (i) an access cannula, (ii) an introducer device including a shaft including a proximal portion that is rigid and a distal portion that is articulable, (iii) a sheath device including a sheath hub and a sheath having a flexible region positioned along the distal portion of the shaft, and (iv) an electrode probe including an electrode hub, an electrode shaft extending from the electrode hub, and a probe near an end of the electrode shaft, the method further including: positioning a distal end of the access cannula within the bone to provide access to an interior region of the bone along a longitudinal axis; directing the shaft of the introducer device and the sheath beyond the access cannula; operating the introducer device to cause the distal portion of the shaft and the flexible region of the sheath to assume a curve within the interior region of the bone; removing the introducer device from the sheath device with the flexible region of the sheath remaining in the curve; directing the electrode shaft through the sheath; exposing the probe beyond the distal end of the sheath; and operating the probe to ablate tissue within the bone.

Clause 26—The method of clause 25, wherein the tissue is the basivertebral nerve.

Clause 27—A spacer lock for a system for augmenting a vertebral body including an access cannula and a treatment device, the spacer lock comprising: a hub defining an aperture sized to receive a shaft of the treatment device, the hub comprising grip surfaces positioned opposite the aperture; legs extending from the hub and configured to be positioned in abutment with the access cannula, wherein the legs define at least one slot; a lock actuator configured to receive an input from a user; and a lock mechanism configured to releasably engage a shaft of the treatment device in response to the lock actuator receiving the input so as to selectively permit movement of the treatment device relative to the spacer lock, wherein the grip surfaces are sized to be engaged by a thumb of a hand to facilitate movement of the treatment device with a syringe-style input.

Clause 28—The spacer lock of clause 27, wherein the grip surfaces are coplanar with one another.

Clause 29—The spacer lock of clauses 27 or 28, wherein the grip surfaces comprise raised features.

Clause 30—The spacer lock of any one of clauses 27-29, wherein the at least one slot is two slots configured to slidably receive a sheath hub of a sheath device.

Clause 31—The spacer lock of any one of clauses 27-30, wherein the aperture is disposed on an axis centered between the legs.

Clause 32—The spacer lock of any one of clauses 27-31, wherein the lock mechanism comprises a torsion spring configured to bias the lock actuator a closed state in which the lock mechanism engages the shaft of the treatment device.

Clause 33—The spacer lock of any one of clauses 27-31, wherein the lock mechanism comprises a disc comprises thinned regions defining slots and an opening, wherein the lock actuator is configured to be in a natural or closed state in which a size of the opening is slightly smaller than an outer diameter of the shaft of the treatment device.

Clause 34—A system for augmenting a vertebral body, the system including: an access cannula including a cannula hub, and a cannula shaft extending from the cannula hub with the cannula shaft including a distal end positionable within the vertebral body and defining a lumen along a longitudinal axis; an introducer device including: an actuator configured to receive an input from a user; a shaft including a proximal portion that is rigid, and a distal portion that is articulable; and a pulling element coupled to the actuator and configured to be tensioned to move the introducer device from an unconstrained state in which the distal portion is oriented along the longitudinal axis, and a constrained state in which the distal portion is configured to assume a curve away from the longitudinal axis, wherein the shaft is removably disposed within a sheath, the sheath including a metal tube having articulating features to define a flexible region configured to extend along the distal portion of the shaft, and a polymeric sleeve coupled to the metal tube and extending between opposing ends of the flexible region, wherein the polymeric sleeve is configured to prevent egress of curable material being delivered through the sheath through the articulating features.

Clause 35—The system of clause 34, wherein the polymeric sleeve is disposed within the metal tube.

Clause 36—The system of clause 34, wherein the metal tube is disposed within the polymeric sleeve.

Clause 37—The system of clause 36, wherein the polymeric sleeve extends over the proximal portion to a sheath hub of the sheath.

Clause 38—The system of any one of clauses 34-37, wherein the polymeric sleeve includes a preformed bend.

Clause 39—The system of any one of clauses 34-38, further including a helical cut pattern within the flexible region of the metal tube.

Clause 40—A sheath device for a system for augmenting a vertebral body, the sheath device including: a sheath hub; and a sheath including a proximal portion extending from the sheath hub along a longitudinal axis and including metal, and a distal portion including polymeric material, wherein the proximal portion is coupled to the distal portion at an interface including a plurality of protrusions on each of the proximal portion and the distal portion configured to engage one another and provide a constant inner diameter and a constant outer diameter across the interface.

Clause 41—The sheath device of clause 40, wherein the plurality of protrusions are disposed equiangularly about the longitudinal axis.

Clause 42—The sheath device of clauses 40 or 41, wherein each of the plurality of protrusions includes a thinned region widening into a bulbous or circular profile.

Clause 43—The sheath device of clauses 40 or 41, wherein each of the plurality of protrusions on the proximal portion includes a barb.

Clause 44—The sheath device of clauses 40 or 41, wherein each of the plurality of protrusions of the proximal portion includes a tine that is wavy in shape.

The foregoing disclosure is not intended to be exhaustive or limit the invention to any particular form. The terminology which has been used is intended to be in the nature of words of description rather than of limitation. Many modifications and variations are possible in light of the above teachings and may be practiced other than as specifically described. The systems and methods may further include placing other height-restoration devices other than balloons, such as those described in U.S. Pat. No. 9,579,130, which is hereby incorporated by reference. The systems and methods may be used to placed components in other bones, beyond vertebral bodies, and may be useful for soft-tissue applications as well, including intradiscal treatment.

The invention claimed is:

1. A system for augmenting a vertebral body, the system comprising:

an access cannula comprising a cannula hub, and a cannula shaft extending from the cannula hub with the cannula shaft comprising a distal end positionable within the vertebral body and defining a lumen along a longitudinal axis;

an introducer device comprising a shaft comprising a distal portion configured to be curved when deployed beyond the distal end of the cannula shaft;

a sheath device comprising a sheath hub, and a sheath extending from the sheath hub, wherein the shaft of the introducer device is removably disposed within the sheath of the sheath device;

a spacer lock configured to facilitate proximal movement of the sheath relative to the access cannula, the spacer lock comprising legs configured to be positioned in abutment with the cannula hub, and defining at least one slot, wherein the sheath hub comprises at least one wing slidably disposed through the at least one slot and configured to be engaged by a finger of a user; and a treatment device comprising a shaft, wherein the spacer lock further comprises a lock mechanism configured to releasably engage the shaft of the treatment device, and wherein the lock mechanism comprises a lock actuator configured to receive an input from the user so as to cause the lock mechanism to releasably engage the shaft of the treatment device and selectively permit movement of the treatment device relative to the sheath device.

2. The system of claim 1, wherein the spacer lock is configured to rest upon the access cannula under influence of gravity without an additional coupling mechanism.

3. The system of claim 1, wherein the lock mechanism comprises a torsion spring configured to bias the lock actuator to a closed state in which the lock mechanism engages the shaft of the treatment device.

4. The system of claim 1, wherein the lock mechanism comprises a disc that comprises thinned regions defining slots and an opening, wherein the lock actuator is configured to be in a natural or closed state in which a size of the opening is slightly smaller than an outer diameter of the shaft of the treatment device.

5. The system of claim 1, wherein the lock mechanism is biased to a closed state.

6. The system of claim 1, wherein the spacer lock further comprises a spacer hub defining an aperture, and grip surfaces oriented radially outwardly from a proximal end of the legs and sized to be engaged by a thumb of a hand to facilitate movement of a treatment device with a syringe-style input.

7. The system of claim 6, wherein the grip surfaces are coplanar with one another.

8. The system of claim 6, wherein the aperture is disposed on an axis centered between the legs.

9. The system of claim 1, wherein the treatment device is one of a cavity-forming device, an electrode probe, a drill, and a biopsy needle.

10. A system for augmenting a vertebral body with a cavity-forming device including a tube and an expandable member coupled to the tube, the system comprising:

an access cannula comprising a cannula hub, and a cannula shaft extending from the cannula hub with the cannula shaft comprising a distal end positionable within the vertebral body and defining a lumen along a longitudinal axis;

an introducer device comprising a shaft comprising a distal portion configured to assume a curve when deployed beyond the distal end of the cannula shaft;

a sheath device comprising a sheath hub, and a sheath extending from the sheath hub, wherein the shaft of the introducer device is removably disposed within the sheath of the sheath device;

a treatment device comprising a shaft and a working end; and a spacer lock comprising a lock mechanism defining an aperture sized to slidably receive the shaft of the treatment device, and wherein the lock mechanism comprises a lock actuator configured to receive an input from a user to selectively permit movement of the shaft of the treatment device relative to the access cannula or the sheath device so as to facilitate unsheathing of the working end of the treatment device.

11. The system of claim 10, wherein the lock mechanism biased to a closed state.

12. The system of claim 10, wherein the spacer lock further comprises legs, and grip surfaces extending radially outwardly from the legs to provide a proximal surface for accommodating a thumb of a hand of the user.

13. A system for augmenting a vertebral body, the system comprising:

an access cannula comprising a cannula hub, and a cannula shaft extending from the cannula hub with the cannula shaft comprising a distal end positionable within the vertebral body and defining a lumen along a longitudinal axis;

an introducer device comprising a shaft comprising a distal portion configured to be curved when deployed beyond the distal end of the cannula shaft;

a sheath device comprising a sheath hub, and a sheath extending from the sheath hub, wherein the shaft of the introducer device is removably disposed within the sheath of the sheath device;

a spacer lock comprising a spacer hub defining an aperture, legs extending from the spacer hub, and grip surfaces oriented radially outwardly from a proximal end the legs and sized to be engaged by a thumb of a hand to facilitate movement of the sheath with a syringe-style input; and a treatment device comprising a shaft and a working end, wherein the shaft of the treatment device is slidably disposed within the aperture, wherein the spacer lock further comprises a lock mechanism configured to releasably engage the shaft of the treatment device, and wherein the lock mechanism comprises a lock actuator configured to receive an input from a user so as to cause the lock mechanism to releasably engage the shaft of the treatment device and facilitate unsheathing of the working end of the treatment device through proximal movement of the sheath with the syringe-style input.

14. The system of claim 13, wherein the grip surfaces are coplanar with one another.

15. The system of claim 13, wherein the aperture is disposed on an axis centered between the legs.

16. The system of claim 13, wherein the treatment device is one of a cavity-forming device, an electrode probe, a drill, and a biopsy needle.

* * * * *